(12) United States Patent
Mantle et al.

(10) Patent No.: US 8,761,874 B2
(45) Date of Patent: Jun. 24, 2014

(54) ELECTRO-OPTICAL TISSUE STIMULATOR AND METHOD OF USE

(76) Inventors: James M. Mantle, Paradise Valley, AZ (US); Murray Edmond Goodman, Paradise Valley, AZ (US)

(*) Notice: Subject to any disclaimer, the term of this patent is extended or adjusted under 35 U.S.C. 154(b) by 485 days.

(21) Appl. No.: 12/902,772

(22) Filed: Oct. 12, 2010

(65) Prior Publication Data

US 2011/0098781 A1    Apr. 28, 2011

Related U.S. Application Data

(60) Provisional application No. 61/255,574, filed on Oct. 28, 2009.

(51) Int. Cl.
*A61N 1/00* (2006.01)
*A61N 1/32* (2006.01)
*A61N 5/06* (2006.01)

(52) U.S. Cl.
CPC ............... *A61N 1/32* (2013.01); *A61N 5/0619* (2013.01); *A61N 2005/0659* (2013.01); *A61N 2005/0651* (2013.01); *A61N 2005/0644* (2013.01)
USPC .................... 607/3; 607/46; 607/88; 607/145

(58) Field of Classification Search
CPC .................... A61N 5/0616; A61N 2005/0644; A61N 2005/0651; A61N 2005/0652
USPC ............................................. 607/46, 88, 145
See application file for complete search history.

(56) References Cited

U.S. PATENT DOCUMENTS

| | | | |
|---|---|---|---|
| 4,694,840 A * | 9/1987 | Kairis et al. | 600/548 |
| 4,977,895 A | 12/1990 | Tannenbaum | |
| 4,989,605 A | 2/1991 | Rossen | |
| 5,024,236 A | 6/1991 | Shapiro | |
| 5,133,352 A | 7/1992 | Lathrop et al. | |
| 5,304,207 A | 4/1994 | Stromer | |

(Continued)

OTHER PUBLICATIONS

Ngok Cheng, M.D., Harry Van Hoof, M.D., Emmanuel Bockx, M.D., Michel J. Hoogmartens, M.D., Joseph C. Mulier, M.D., Frans J. De Dijcker, Ph.D., Willy M. Sansen, Ph.D., and William De Loecker, M.D.; The Effects of Electric Current on ATP Generation, Protein Synthesis, and Membrane Transport in Rat Skin; Clinical Orthopaedics and Related Research; Nov.-Dec. 1982, pp. 264-272; J.B. Lippincott Co.

(Continued)

*Primary Examiner* — Allen Porter, Jr.
(74) *Attorney, Agent, or Firm* — Schmeiser, Olsen & Watts LLP

(57) ABSTRACT

An electro-optical tissue stimulator for administering therapy to a body is disclosed comprising a housing and an active tip. The electro-optical tissue stimulator includes a microcurrent electrostimulation therapy unit which delivers current through a first and a second electrode in the active tip. The electro-optical tissue stimulator also includes an optical radiation therapy unit which delivers optical radiation through a light output port in the active tip. The active tip is shaped for administering myofascial tissue release therapy. The device can administer microcurrent electrostimulation therapy, optical radiation therapy, and myofascial tissue release therapy to tissues of a body. A method of treating pain is disclosed which includes the steps of identifying a treatment area on a body to receive therapy, and contacting the treatment area with the active tip, wherein the treatment area receives microcurrent electrostimulation therapy, optical radiation therapy, and myofascial tissue release therapy.

6 Claims, 9 Drawing Sheets

(56) References Cited

U.S. PATENT DOCUMENTS

| | | |
|---|---|---|
| 5,620,481 A | 4/1997 | Desai et al. |
| 6,249,698 B1 * | 6/2001 | Parris ................................ 607/3 |
| 7,198,633 B1 * | 4/2007 | Starwynn ........................ 607/90 |
| 7,321,428 B2 | 1/2008 | Hunt et al. |
| D588,696 S | 3/2009 | Mantle et al. |
| 2006/0200211 A1 * | 9/2006 | Lin ................................. 607/88 |
| 2006/0282134 A1 * | 12/2006 | Shapiro et al. .................. 607/88 |
| 2009/0234423 A1 | 9/2009 | Vetanze |

OTHER PUBLICATIONS

Tiziano Marovino, PT, DPT MSC, BA, BHSC, BRLS, DIP. PT,FAAPM; Pain Management; Practical Pain Management; Sep./Oct. 2004, pp. 37-42.

* cited by examiner

ELECTRO-OPTICAL TISSUE STIMULATOR AND METHOD OF USE

CROSS REFERENCE TO RELATED APPLICATION

This application claims priority to U.S. Provisional Patent Application to James M. Mantle entitled "Electro-Optical Tissue Stimulator and Method of Use," Ser. No. 61/255,574, filed Oct. 28, 2009, the disclosure of which is hereby incorporated entirely herein by reference.

BACKGROUND OF THE INVENTION

1. Technical Field

This invention relates generally to devices used for alleviating pain in the body and more particularly to the use of electrical current, optical radiation, and myofascial tissue pressure for the reduction of pain.

2. State of the Art

Methods for reducing pain in the body are in constant demand. Pain in the body can be acute or chronic as a result of injury, disease, surgery, physical overexertion, or often of unknown origin. Common treatments for pain can include physical therapy, surgery, or drugs. Drugs mask or block the feeling of pain and allow the person to function pain-free. Aspirin and other pain-relief drugs are a common source of relief of pain. If the pain cannot be relieved through the use of over-the-counter drugs, the person experiencing the pain can resort to prescribed stronger drugs. Other medical treatments which can be used to alleviate pain by masking or blocking the pain signal include treatments such as epidurals, nerve blocks, trigger point injections, and nerve ablations. Pain relief drugs and pain-blocking surgery may or may not be effective and are not preferred solutions due to the fact that they do not eliminate the pain but instead block or mask the pain signal. The bodily condition which is the source of the pain remains unchanged even though the pain may have been relieved.

If the source of the sense of pain can be identified and is correctable by surgery, then surgical relief can be used to fix the problem and relieve the pain. In many cases, however, the source of pain cannot be fixed by surgery or cannot be identified at all. Surgery itself has its risks and is not a preferred treatment for pain if other treatments are available.

Various types of physical therapy have been developed in an attempt to eliminate pain in the body. Physical therapy is preferred by some individuals because it does not necessarily involve the use of drugs, is non-surgical, and does not block the pain signal but instead tries to help the body heal itself and fix the tissue generating the pain, which results in a reduction or elimination of the pain. Physical therapy has many forms, depending on the type and placement of the pain, but can include exercise, stretching, heat or cold therapy, and muscle massage. It is believed by some that delivering transcutaneous energy in the form of optical radiation or electrical current may have therapeutic benefits to the body, particularly to alleviate pain. In addition, myofascial tissue release therapy, which is a method of soft tissue massage which acts on the fascia, a web in the body which interconnects muscles, tissues, and organs, may help reduce musculo-skeletal pain. These types of therapy are usually administered separately, often by a doctor or therapist. Thus while these techniques are safe and suitable for home use and administration the need of a specialist often renders home application impractical or unaffordable. Further, successful results often depend upon frequent treatments. Accordingly, it is desirable to have a device for administering these types of therapy at home without the need for a specialist. It is also desirable to have a single device which can provide all of these types of therapy in one device.

Hence a novel device is described which can provide multiple forms of pain relief therapy in a single device, especially microcurrent electrostimulation therapy, optical radiation therapy, and myofascial tissue release therapy. This device can be used by a doctor, a therapist, or the individual desiring treatment, at a treatment center or at home. A method of using the device is described which provides pain relief benefits from multiple types of therapy.

DISCLOSURE OF THE INVENTION

The present invention relates to methods for relieving bodily pain, and more specifically to the use of electrical current, optical radiation, and myofascial tissue pressure for the reduction of pain. An electro-optical tissue stimulation device for administering therapy to a body is disclosed which includes a housing and an active tip. The device includes a microcurrent electrostimulation therapy unit which delivers current through a first and a second electrode mounted in the active tip. The device also includes an optical radiation therapy unit which delivers optical radiation through a light output port mounted in the active tip. The active tip is shaped for administering myofascial tissue release therapy to a body. The electro-optical tissue stimulation device includes an output level adjustor which allows independent adjustment of both the electrical current level delivered by the microcurrent electrostimulation therapy unit and the optical radiation level delivered by the optical radiation therapy unit. The device can administer microcurrent electrostimulation therapy, optical radiation therapy, and myofascial tissue release therapy to tissues of the body. These three types of therapy can be delivered simultaneously, individually or in pairs. In some embodiments the device includes a wavelength adjustor which adjusts the wavelength of the optical radiation delivered by the optical radiation therapy unit. In some embodiments the device includes an electrical current duty cycle adjustor. In some embodiments the device includes an optical radiation duty cycle adjustor. In some embodiments the electro-optical tissue stimulator includes an electrical current duty cycle adjustor. In some embodiments the light output port is positioned between the first and the second electrode. In some embodiments the device includes an output phase adjustor.

A method of treating pain is disclosed which comprises the steps of identifying a treatment area on a body to receive electro-optical tissue stimulation therapy and activating an electro-optical tissue stimulator, wherein the electro-optical tissue stimulator comprises an active tip. The method also includes contacting a test area of the body with the active tip, wherein the test area of the body is not a part of the treatment area of the body. The method also includes the step of setting the power output level of the electro-optical tissue stimulator to a level where the test area of the body begins to feel a tingling sensation in response to contact by the active tip. The method further comprises contacting the treatment area with the active tip, wherein the treatment area receives microcurrent electrostimulation therapy, optical radiation therapy, and myofascial tissue release therapy in response to contact by the active tip. Some embodiments of the method of treating pain include the step of setting the wavelength of the optical radiation output of the electro-optical tissue stimulator. Some embodiments of the method include setting the output duty cycle of the optical radiation delivered by the electro-optical tissue stimulator. Some embodiments of the method include setting the output duty cycle of the electrical current delivered by the electro-optical tissue stimulator. Some embodiments of the method of treating pain include the step of setting the relative phase of the optical radiation and the electrical current delivered by the electro-optical tissue stimulator. Some embodiments include the steps of recording and/or testing a level of disability, pain, flexibility, range of motion, or mobility before administering therapy. Some embodiment include the steps or recording and/or testing a level of disability, pain, flexibility, range of motion, or mobility after administering therapy. Some embodiments include the steps of measuring the effectiveness of treatment using the data from before and after testing. Some embodiments of this method of treating pain include applying a conductive gel to the treatment area before contact with the active trip.

A method of administering therapy to a body is disclosed which includes the steps of identifying a treatment area of a body to receive therapy from an electro-optical tissue stimulator, wherein the electro-optical tissue stimulator comprises an active tip, and determining the desired optical radiation output level of the electro-optical tissue stimulator. The method of administering therapy to a body also includes the steps of determining the desired electrical current output level of the electro-optical tissue stimulator, and setting the optical radiation output level of the electro-optical tissue stimulator to the desired optical radiation output level. The method of administering therapy to a body includes the step of administering myofascial tissue release therapy to the treatment area using the active tip, wherein the treatment area receives microcurrent electrostimulation therapy, optical radiation therapy, and myofascial tissue release therapy in response to administering myofascial tissue release therapy with the active tip. In some embodiments the method includes the step of setting the electrical current output level of the electro-optical tissue stimulator to the desired electrical current output level. In some embodiments other forms of therapy are administered with the active tip. In some embodiments of the method for administering therapy to a body according to the invention, the step of determining the desired optical radiation output level of the electro-optical tissue stimulator further includes the steps of setting the electrical current output level of the electro-optical tissue stimulator to zero, contacting a test area of the body with the active tip, wherein the test area is not included in the treatment area, and adjusting the optical radiation output level until the desired optical radiation output level of the electro-optical tissue stimulator is determined, wherein the desired optical radiation output level is that level where a tingling sensation is beginning to be felt in the test area in response to the test area receiving optical radiation from the active tip. In some embodiments of the method for administering therapy to a body according to the invention, the step of determining the desired electrical current output level of the electro-optical tissue stimulator further includes the steps of setting the optical radiation output level of the electro-optical tissue stimulator to zero, contacting a test area of the body with the active tip, wherein the test area is not included in the treatment area, and adjusting the electrical current output level until the desired electrical current output level of the electro-optical tissue stimulator is determined, wherein the desired electrical current output level is that level where a tingling sensation is beginning to be felt in the test area in response to the test area receiving electrical current from the active tip A method of conducting business is disclosed comprising the steps of developing techniques for administering therapy utilizing an electro-optical tissue stimulator, marketing the electro-optical tissue stimulator, and selling the electro-optical tissue stimulator to doctors. This method can include selling the electro-optical tissue stimulator to patients. In some embodiments this business method includes designing an electro-optical tissue stimulator. In some embodiments manufacturing an electro-optical tissue stimulator is included.

The foregoing and other features and advantages of the present invention will be apparent from the following more detailed description of the particular embodiments of the invention, as illustrated in the accompanying drawings.

DETAILED DESCRIPTION OF EMBODIMENTS OF THE INVENTION

As discussed above, embodiments of the present invention relate to methods to relieve pain in the body, and more specifically to methods for reducing pain using electrical stimulation, optical radiation, or myofascial tissue pressure.

Figure 1:
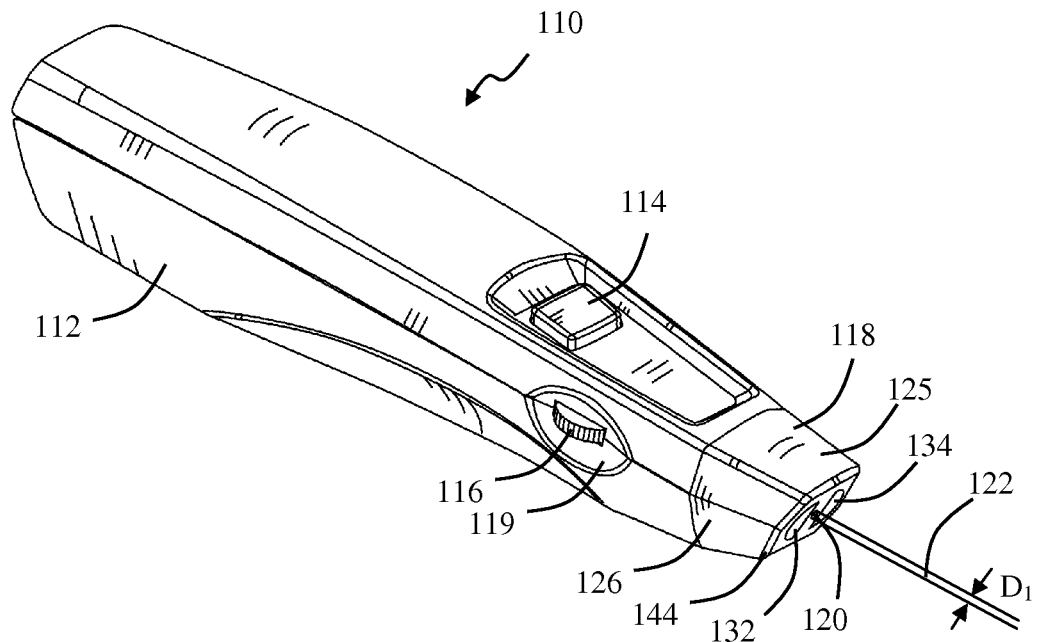
FIG. 1 is a front perspective view of an embodiment of electro-optical tissue stimulator 110 according to the present invention.
Figure 2:
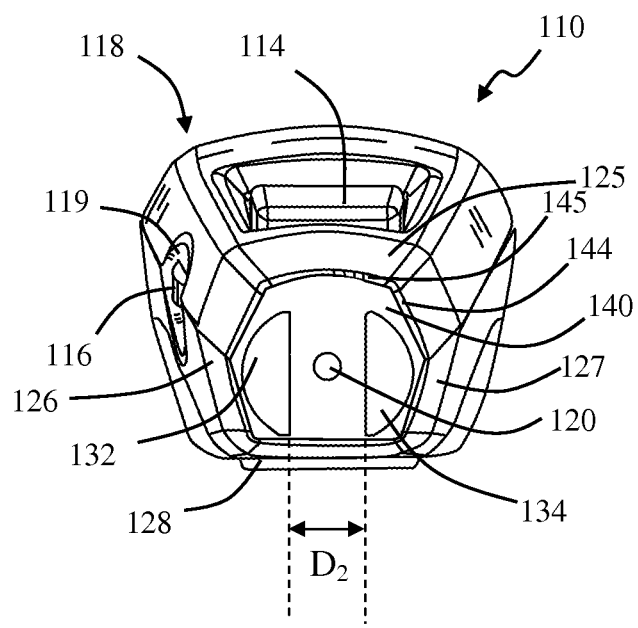
FIG. 2 is a front end view of electro-optical tissue stimulator 110 of FIG. 1.
Figure 3:
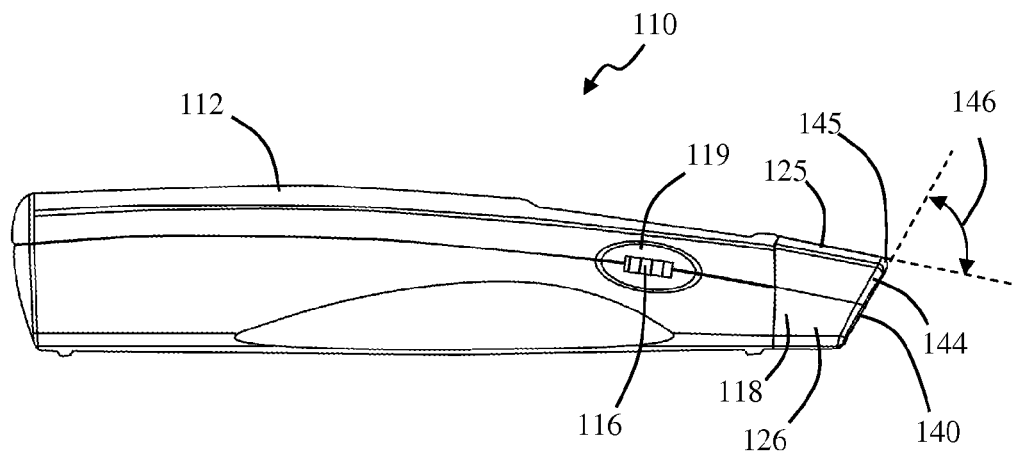
FIG. 3 is a side view of electro-optical tissue stimulator 110 of FIG. 1.
Figure 4:
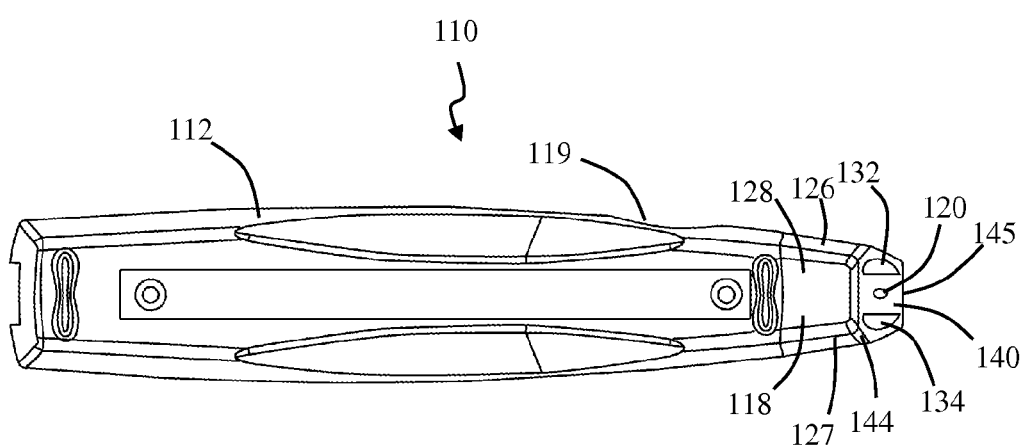
FIG. 4 is a bottom view of electro-optical tissue stimulator 110 of FIG. 1.

FIG. 1 through FIG. 4 show various views of one embodiment of electro-optical tissue stimulator 110 according to the invention, which is capable of administering multiple types of pain-relief therapy to tissues of the body, including microcurrent electrostimulation therapy, optical radiation therapy, and myofascial tissue release therapy. FIG. 1 shows a perspective view of electro-optical tissue stimulator 110 according to the invention. FIG. 2 shows a front end view of electro-optical tissue stimulator 110 of FIG. 1, FIG. 3 shows a side view of electro-optical tissue stimulator 110 of FIG. 1, and FIG. 4 shows a bottom view of electro-optical tissue stimulator 110 of FIG. 1. Electro-optical tissue stimulator 110 delivers transcutaneous energy in the form of optical radiation, electrical current, and myofascial tissue pressure to portions of the body for the purpose of relieving pain. Electro-optical tissue stimulator 110 is often battery-powered and hand-held. Electro-optical tissue stimulator 110 has active tip 118 on one end for delivering multiple forms of therapy by placing tip 118 on the skin of a subject or patient and delivering therapy using one or all of the multiple types of therapy that electro-optical tissue stimulator 110 is capable of administering. Electro-optical tissue stimulator 110 stimulates bodily tissues with electrical current and optical radiation and myofascial tissue pressure. These types of tissue stimulation facilitate the body's own ability to repair and heal, which can often result in pain reduction, increased range of motion, and increased mobility. Electro-optical tissue stimulator 110 can be used on chronic intractable pain of musculo-skeletal origin and post-traumatic and post-surgical pain. Electro-optical tissue stimulator 110 does not block pain, but reduces pain by helping the bodily tissues heal. Electro-optical tissue stimulator 110 provides the ability to administer these various forms of therapy individually or in combinations or simultaneously, increasing the treatment options available. Therapy can be administered by a doctor or professional therapist using electro-optical tissue stimulator 110 or by the patient themselves. Electro-optical tissue stimulator 110 can often be used by the patient themselves at the doctor's office or at the patient's home.

Figure 5:
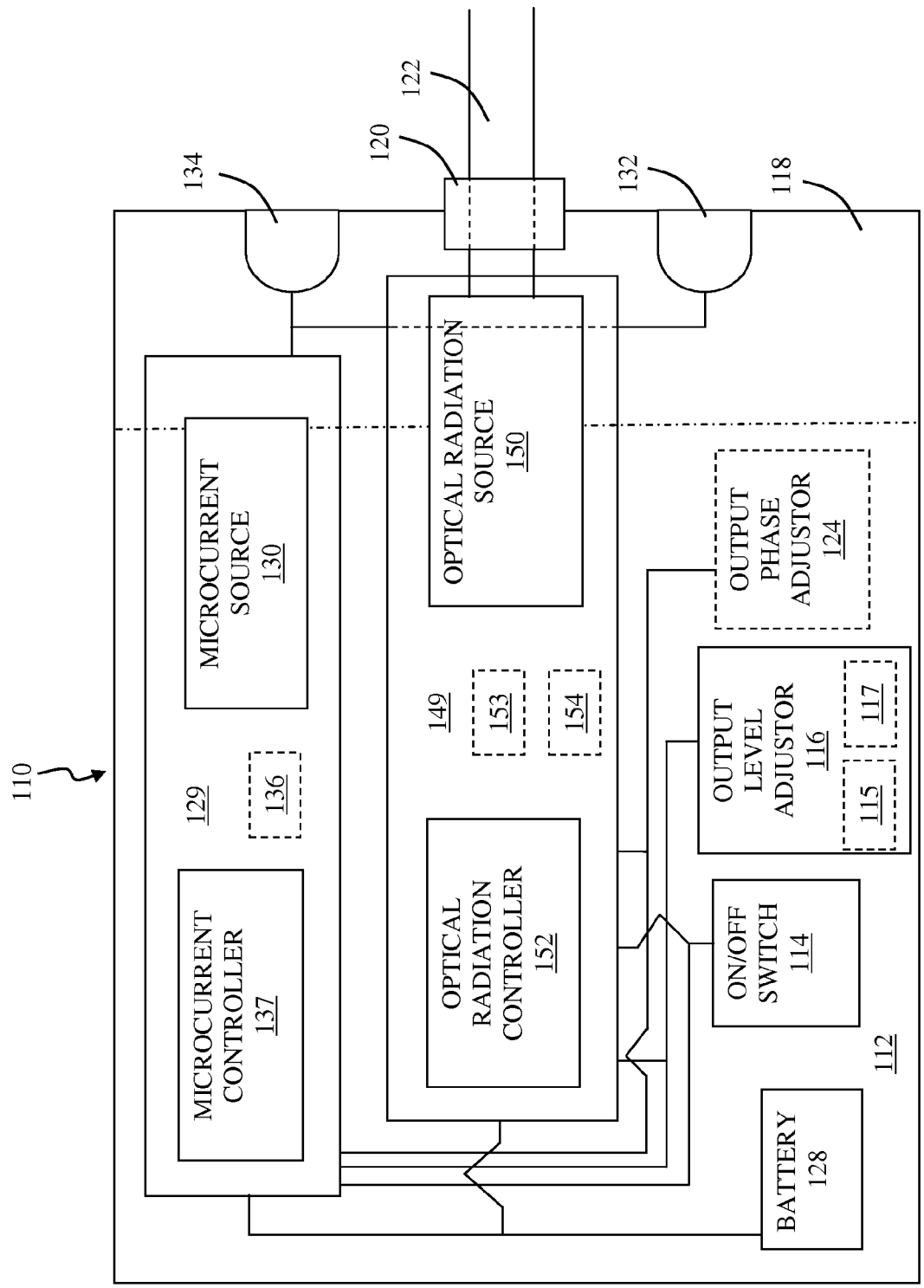
FIG. 5 is a block diagram illustrating components of electro-optical tissue stimulator 110 of FIG. 1.
Figure 6:
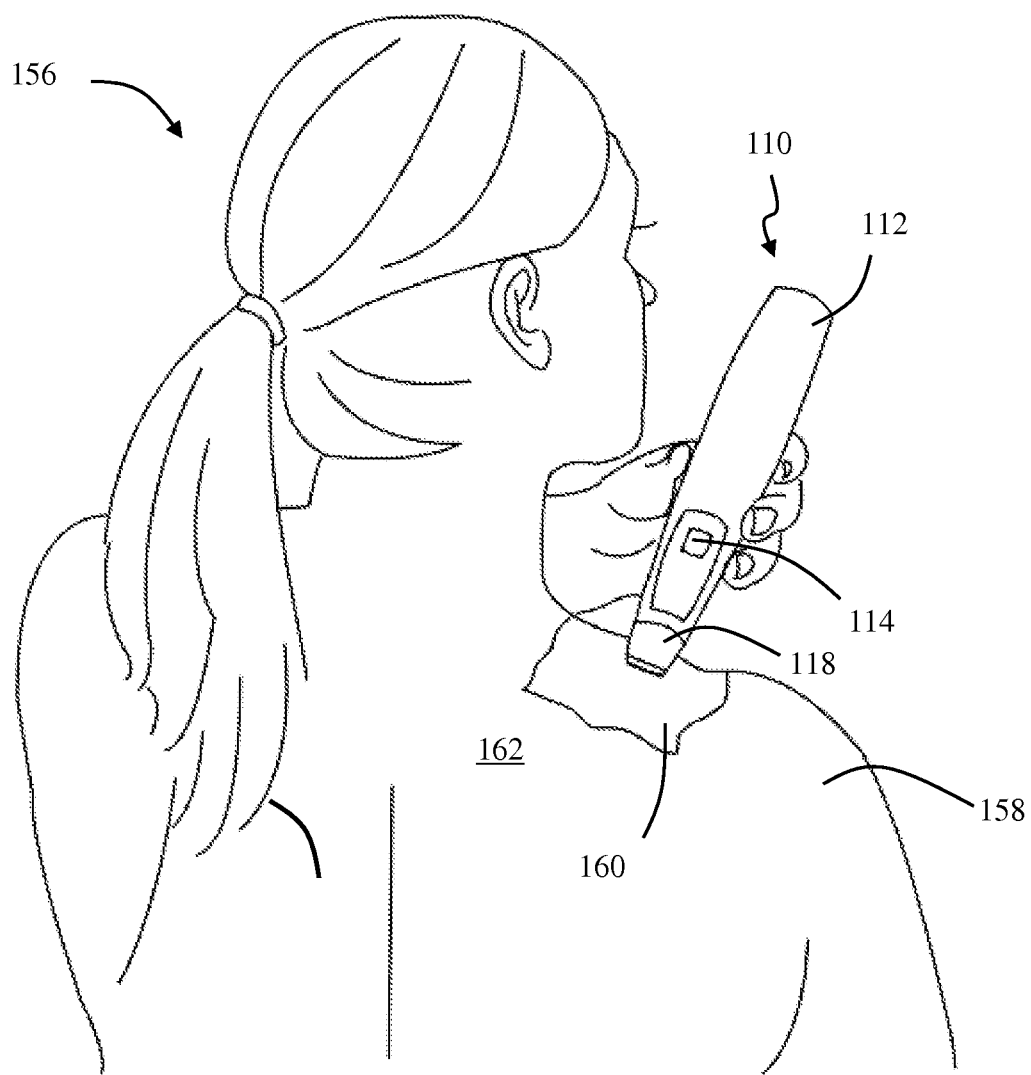
FIG. 6 is a perspective view of person 156 administering therapy to a portion of body 158 using electro-optical tissue stimulator 110 according to the present invention.
Figure 7:
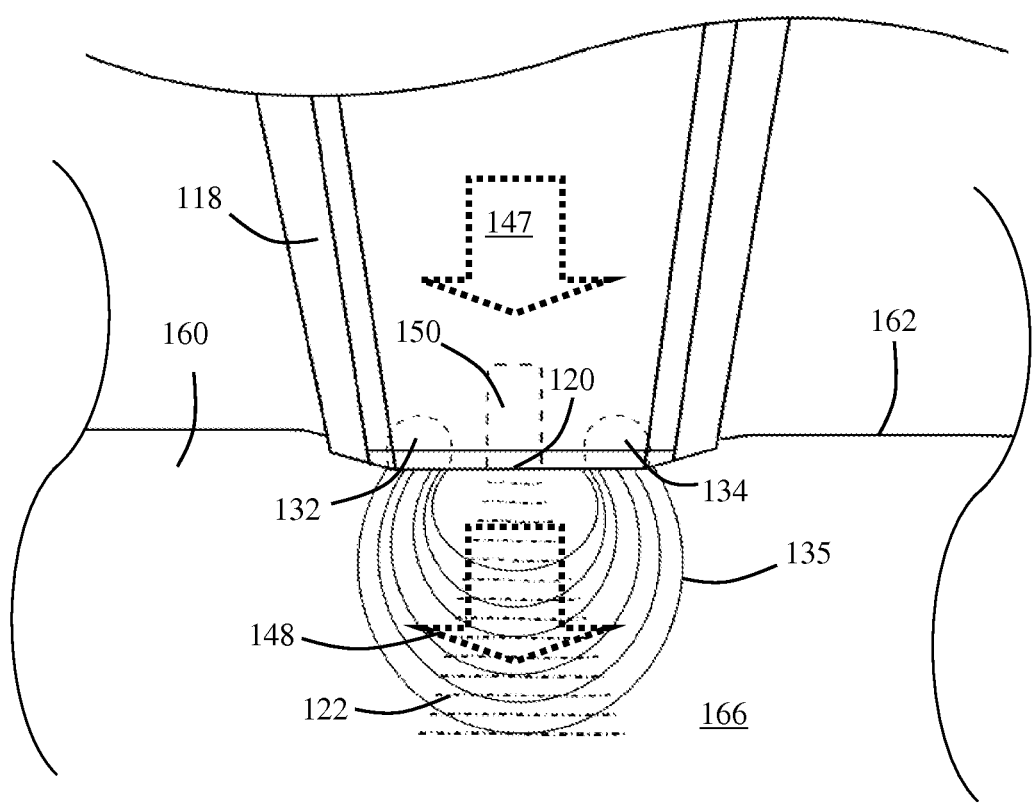
FIG. 7 shows a cross-section of treatment area 160 illustrating how active tip 118 of electro-optical tissue stimulator 110 according to the invention delivers microcurrent electrostimulation therapy, optical radiation therapy, and myofascial tissue release therapy to tissue 166 according to the invention.
Figure 8:
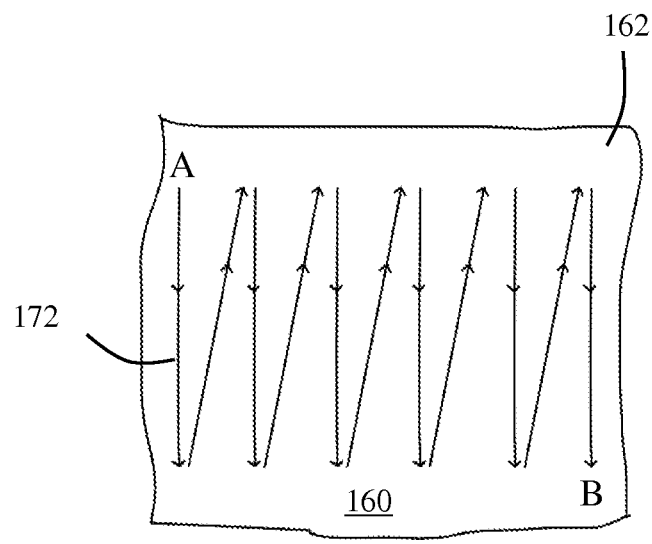
FIG. 8 is a top view of a pattern of motion 172 of electro-optical tissue stimulator 110 across skin 162 of treatment area 160 which can be used in administering therapy using electro-optical tissue stimulator 110 according to the invention.
Figure 9:
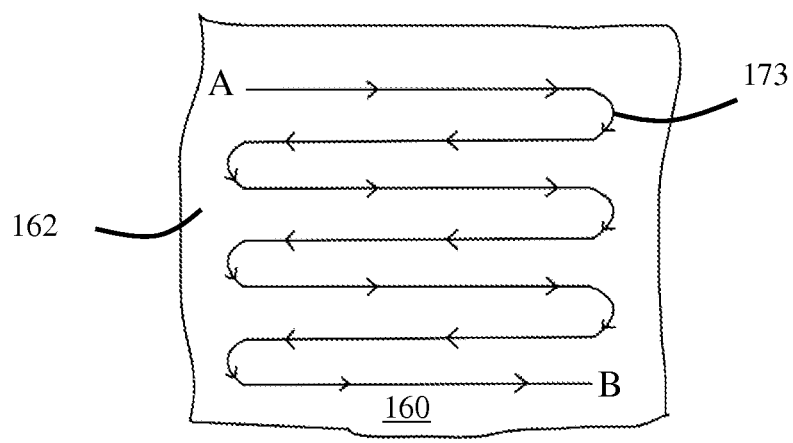
FIG. 9 is a top view of a pattern of motion 173 of electro-optical tissue stimulator 110 across skin 162 of treatment area 160 which can be used in administering therapy using electro-optical tissue stimulator 110 according to the invention.
Figure 10:
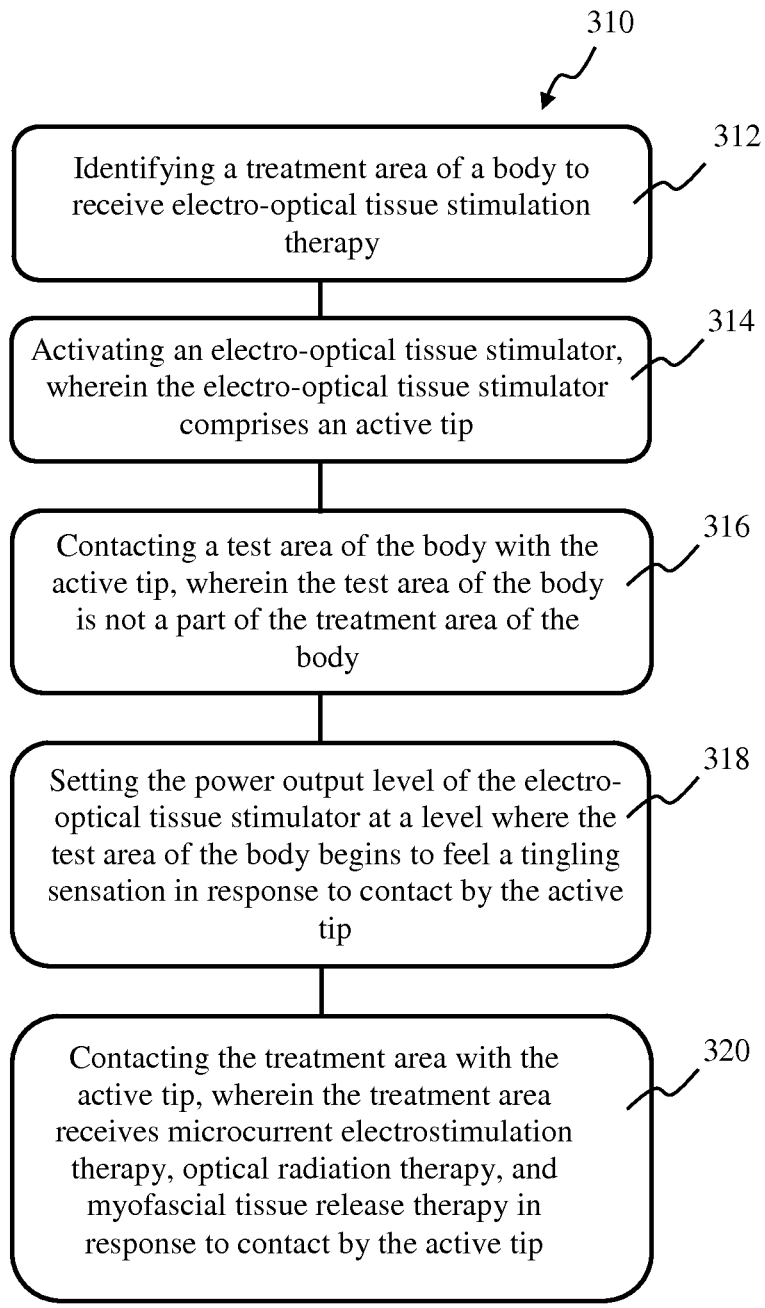
FIG. 10 illustrates method of treating pain 310 according to the invention.
Figure 11:
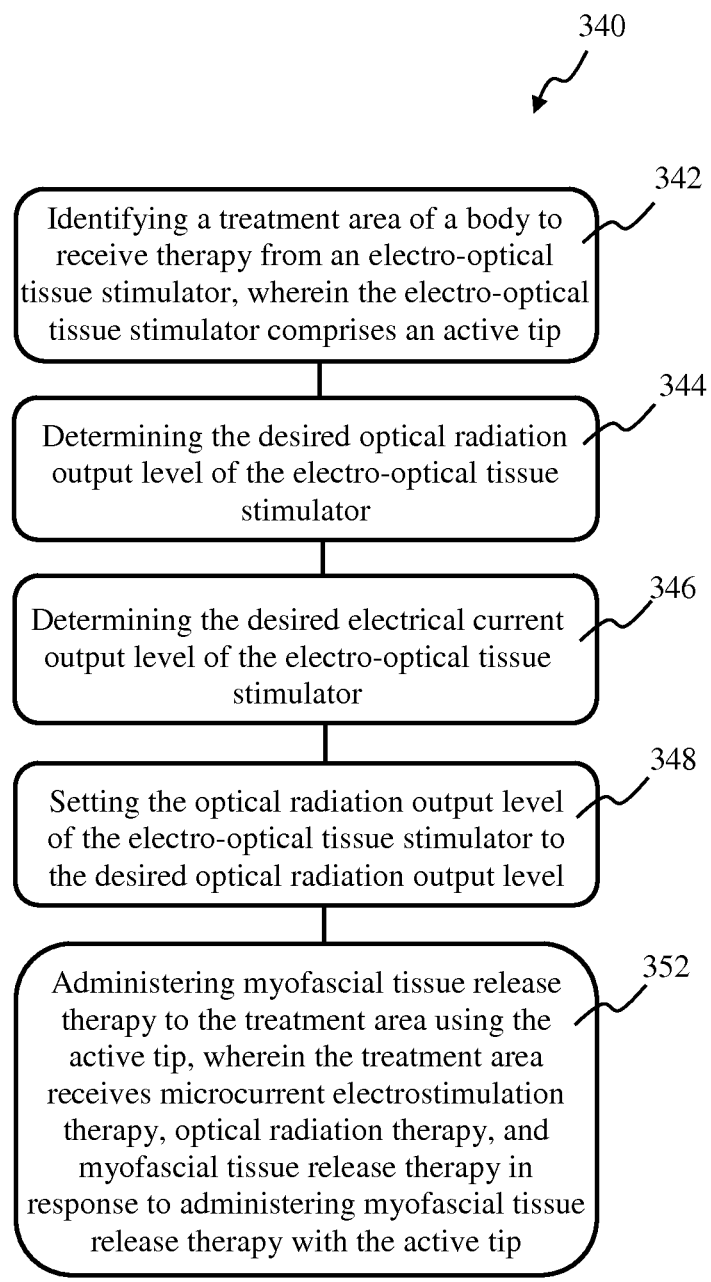
FIG. 11 illustrates method of administering therapy 340 according to the invention.
Figure 12:
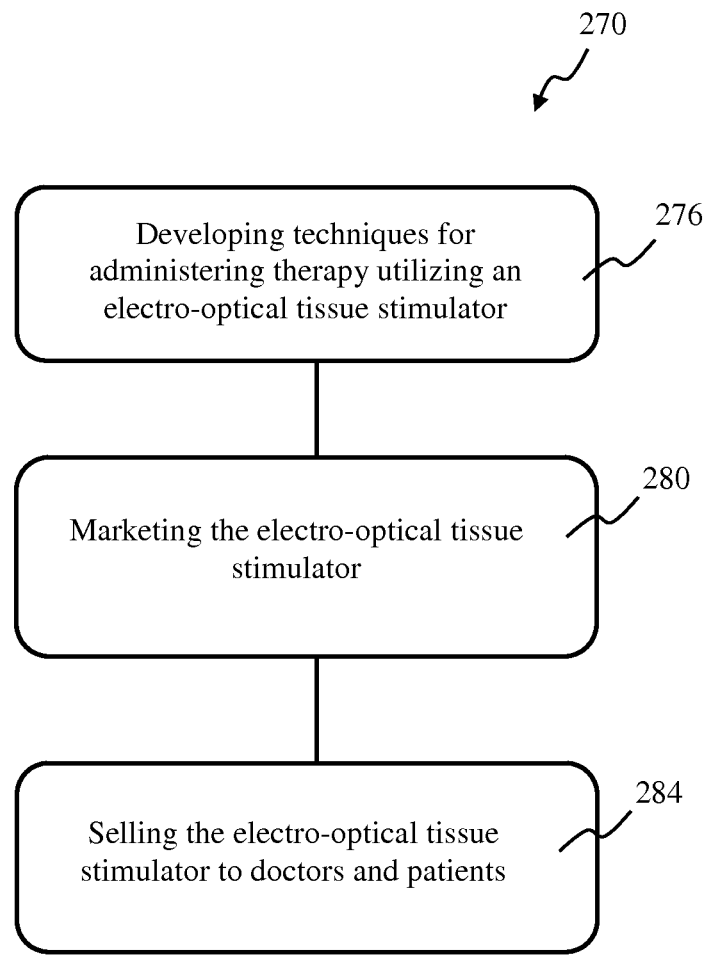
FIG. 12 illustrates method of conducting business 270 according to the invention.

FIG. 5 shows a block diagram of some of the components of electro-optical tissue stimulator 110. FIG. 6 shows electro-optical tissue stimulator 110 being used by person 156 on treatment area 160 of body 158. FIG. 7 is a cross section of treatment area 160 of body 158 illustrating how active tip 118 of electro-optical tissue stimulator 110 administers transcutaneous current 135, optical radiation 122, and myofascial tissue release pressure 148 for the purpose of providing pain relief therapy to tissues 166. FIG. 8 and FIG. 9 show patterns of movement of electro-optical tissue stimulator 110 over treatment area 160 which can be used with the disclosed method of treatment to administer therapy to treatment area 160. FIG. 10 shows a method of treating pain according to the invention using electro-optical tissue stimulator 110. FIG. 11 shows a method of administering therapy according to the invention, and FIG. 12 shows a method of conducting business according to the invention.

Electro-optical tissue stimulator 110 according to the invention as shown in FIGS. 1-4 includes housing 112 and active tip 118. In this embodiment housing 112 contains the components of electro-optical tissue stimulator 110 shown in FIG. 5. Optional components of electro-optical tissue stimulator 110 are shown in dashed lines in FIG. 5. The dot-dash line in FIG. 5 separates active tip 18 from the remainder of housing 112. Active tip 118 is the portion of electro-optical tissue stimulator 110 which contacts skin 162 to deliver therapy or treatment. In this embodiment the components within electro-optical tissue stimulator 110 include microcurrent electrostimulation therapy unit 129, and optical radiation therapy unit 149. In some embodiments other components and therapy devices are included in electro-optical tissue stimulator 110. In some embodiments an ultrasound therapy unit is included. In other embodiments a heat therapy unit is included in electro-optical tissue stimulator 110. Any of numerous devices and units can be included in electro-optical tissue stimulator 110 that are consistent with the bodily therapy use of electro-optical tissue stimulator 110.

Microcurrent electrostimulation therapy unit 129 includes microcurrent controller 137, microcurrent source 130, and contact electrodes 132 and 134. Contact electrodes 132 and 134 reside on the outer surface of active tip 118 so they can simultaneously contact skin 162. Microcurrent electrostimulation therapy unit 129 delivers electrical current 135 through first electrode 132 and second electrode 134 mounted in active tip 118. Electrodes 132 and 134 deliver current 135 to body tissue 166 when electrodes 132 and 134 are in an activated state (receiving power) and in contact with skin 162 of body 158 (see FIG. 6 and FIG. 7). In this embodiment electrodes 132 and 134 are on flat face 140 of active tip 118, with distance $D_2$ between them (see FIG. 2). In this embodiment electrodes 132 and 134 are made of stainless steel. In some embodiments electrodes 132 and 134 are made of other conductive materials. More details of microcurrent electrostimulation therapy unit 129 will be provided shortly.

Optical radiation therapy unit 149 includes optical radiation controller 152, optical radiation source 150, and light output port 120. When optical radiation source 150 is powered it emits (delivers) optical radiation 122 (also referred to as light beam 122), through light output port 120. Optical radiation 122 delivered through light output port 120 can subsequently impinge skin 162. Light output port 120 is, in this particular embodiment, in active tip 118 between electrodes 132 and 134 (see FIG. 1 and FIG. 2). Optical radiation therapy unit 149 delivers optical radiation 122 through light output port 120 mounted in active tip 118. In this embodiment electrodes 132 and 134 and light output port 120 are positioned so that current 135 and optical radiation 122 are incident on the same or overlapping portions of skin 162. In this way the portion of treatment area 160 which receives microcurrent electrostimulation therapy overlaps the portion of treatment area 160 which receives optical radiation therapy. In some embodiments of electro-optical tissue stimulator 110 electrodes 132 and 134 and light output port 120 are positioned such that current 135 and optical radiation 122 are incident on non-overlapping portions of skin 162. In the embodiment shown in FIG. 1 through FIG. 4, optical radiation source 150 is a single red laser diode which makes optical radiation 122 a red laser beam. Optical radiation source 150 can be many different types, as will be described later. Optical radiation source 150 can, in some embodiments, be composed of multiple light emitting devices. More details of optical radiation therapy unit 149 will be provided shortly.

Myofascial tissue release therapy is administered using flat face 140 and pointed area 145 of active tip 118 (see FIG. 3) Flat face 140 and pointed area 145 of active tip 118 are shaped to administer myofascial tissue release therapy by applying pressure 148 to skin 162 and underlying tissue 166, as shown in FIG. 7. More details of myofascial tissue release therapy provided by active tip 118 will be provided shortly.

Electro-optical tissue stimulator 110 comprising microcurrent electrostimulation therapy unit 129 and optical radiation therapy unit 149 is powered in this embodiment by battery 128. In some embodiments electro-optical tissue stimulator 110 may not be battery-powered. Some embodiments of electro-optical tissue stimulator 110 may include therapy units which require more power than that deliverable by a battery. Some embodiments of electro-optical tissue stimulator 110 may be designed to deliver power levels of microcurrent electrostimulation or optical radiation which cannot be supplied by battery power. For these embodiments electro-optical tissue stimulator 110 can receive wall plug power. While it is desirable to have electro-optical tissue stimulator 110 be battery-powered for ease of use and portability, embodiments of the invention disclosed herein can be wall-plug-powered or powered by other power sources. Whether electro-optical tissue stimulator 110 is battery powered or wall-plug-powered or otherwise powered, housing 112 should be small enough for therapy to be administered manually.

Electro-optical tissue stimulator 110 includes on/off switch 114, which in this embodiment turns power on and off to both microcurrent electrostimulation therapy unit 129 and optical radiation therapy unit 149. Tuning power on is also referred to as 'activating' in this document. On/off switch 114 is used to activate electro-optical tissue stimulator 110, which in this embodiment activates—or turns power on to—both microcurrent electrostimulation unit 129 and optical radiation therapy unit 149. In some embodiments electro-optical tissue stimulator 110 includes other powered therapy units which have their power turned on and off using power switch 114. In some embodiments microcurrent electrostimulation therapy unit 129 and optical radiation therapy unite 149 have their own individual power switches so that they can be activated, or turned on and off, separately from each other. A feature of electro-optical tissue stimulator 110 is that it can provide different forms of therapy together or separately. This allows the type of therapy administered to be tailored to the needs of the specific condition being treated.

Electro-optical tissue stimulator 110 includes output level adjustor 116 mounted in housing 112. In this embodiment output level adjustor 116 is mounted in recess 119 of housing 112. Output level adjustor 116 is positioned in recess 119 to minimize accidental engagement with output level adjustor 116 during treatment. Output level adjustor 116 adjusts the level of optical radiation 122 and electrical current 135 delivered (output) by electro-optical tissue stimulator 110. Output level adjustor 116 is used to set, or adjust, the power output level of electro-optical tissue stimulator 110, where the power output level includes the level of optical radiation 122 and the level of electrical current 135 that is output, or delivered, by electro-optical tissue stimulator 110. In this embodiment output level adjustor 116 adjusts the output level of both microcurrent electrostimulation therapy unit 129 and optical radiation therapy unit 149 simultaneously. Output level adjustor 116 adjusts the electrical current output level of current 135 delivered by electrodes 132 and 134 higher and lower as output level adjustor 116 is adjusted higher and lower respectively. Output level adjustor 116 adjusts the optical radiation output level of light beam 122 higher and lower as output level adjustor 116 is adjusted higher and lower respectively. In some embodiments microcurrent electrostimulation therapy unit 129 and optical radiation therapy unit 149 have their own individual output level adjustment switches. In a particular embodiment output level adjustor 116 includes electrical current output level adjustor 117, which allows independent adjustment of the level of electrical current 135 delivered by microcurrent electrostimulation therapy unit 129, and optical radiation output level adjustor 115, which allows independent adjustment of the level of optical radiation 122 delivered by optical radiation therapy unit 149. Electrical current output level adjustor 117 of output level adjustor 116 allows the level of electrical current 135 to be adjusted up or down without affecting the level of optical radiation 122. Optical radiation output level adjustor 115 of output level adjustor 116 allows the level of optical radiation 122 to be adjusted up or down without affecting the level of electrical current 135. In some embodiments electro-optical tissue stimulator 110 includes other powered therapy units which may have their own power output level switch or may share power output level adjustor 116.

Microcurrent electrostimulation therapy unit 129 provides pain relief by passing low levels of electrical current through body tissue 166, which stimulates tissue growth and repair, resulting in a reduction of pain. Microcurrent electrostimulation as used here is sometimes referred to by different names in literature. The term microcurrent electrostimulation as used here includes the forms of therapy referred to as microcurrent electrical biostimulation, transcutaneous electrical neural stimulation, micro-current electrical stimulation, and transcutaneous electrical nerve stimulation, among others. In general this type of therapy delivers transcutaneous energy in the form of electrical current to the tissues of the body as a remedial treatment, usually for the reduction of pain. Transcutaneous means "through the skin". As shown in FIG. 7, current 135 is administered to body tissue 166 by passing through skin 162 into tissue 166. No surgery or cutting of skin 162 is involved.

Current 135 is provided by microcurrent source 130, which is controlled by microcurrent controller 137 as shown in FIG. 5. Microcurrent source 130, when activated by turning power switch 114 to the 'on' state, energizes (or makes active, turns on) electrodes 132 and 134 in active tip 118. When electrodes 132 and 134 are energized and come into contact with skin 162, current 135 passes through skin 162 and into tissue 166, following the electrical circuit path between electrode 132 and 134, as shown in FIG. 7. In this way microcurrent electrostimulation therapy unit 129 delivers electrical current 135 through first electrode 132 and second electrode 134 mounted in active tip 118. Tissue 166 responds favorably to current 135 passing through it. The benefits have been shown to include reduction of pain in tissue 166. There are many possible specific circuit implementations of microcurrent source 130 and microcurrent controller 137, which can result in different specific implementations of microcurrent electrostimulation therapy unit 129.

The amount of current 135 delivered (output) by microcurrent electrostimulation therapy unit 129 is referred to as the electrical current output level or current output level. The current output level is generally less than one amp, typically in the microamp range. In some embodiments the current is about 10 microamps. In some embodiments the current is about 1000 microamps. In a specific embodiment the current is about 6 milliamps. Current 135 can be a direct current (DC) or an alternating current (AC). Current 135 can alternate at many different frequencies. In some embodiments electro-optical tissue stimulator 110 includes an electrical current frequency adjustor, which is an apparatus which allows the frequency of current 135 delivered by microcurrent electrostimulation therapy unit 129 to be adjusted within a range of available frequencies. In some embodiments the frequency range used is from 10 kilohertz (KHz) to 19 KHz.

Current 135 can also be pulse-width modulated (pwm), which means the current will alternate between being "on" and being "off" at a specific frequency. The frequency used for pwm of current 135 can vary depending on the specific implementation and the type of therapy desired as is known in the art. In some embodiments electro-optical tissue stimulator 110 includes electrical current duty cycle adjustor 136, which adjusts the duty cycle, or relative time the current is "on" compared to the relative time the current is "off" of microcurrent electrostimulation therapy unit 129. Pulsing current 135 at different duty cycles can be used to provide treatment to specific types of tissues 166 as desired. Electrical current duty cycle adjustor 136 is used to set the output duty cycle of electrical current 135 that is delivered by electro-optical tissue stimulator 110.

Any of the various specific circuit implementations known in the art to provide microcurrent electrostimulation can be used in this invention, provided it can be implemented in a hand-held device. Electro-optical tissue stimulator 110 is held manually against skin 162 of body 158 as shown in FIG. 6. Microcurrent electrical stimulation therapy is administered in response to microcurrent electrostimulation therapy unit 129 of electro-optical tissue stimulator 110 being activated, and active tip 118 being held against skin 162. Skin 162 completes the electrical circuit between electrode 132 and 134, which allows current 135 to pass through tissue 166. In this way treatment area 160 receives microcurrent electrostimulation therapy in response to microcurrent electrostimulation therapy unit 129 being activated and contact being made by active tip 118 to treatment area 160. FIG. 6 shows person 156 administering therapy to themselves using electro-optical tissue stimulator 110. In some embodiments another individual, who can be a doctor or therapist, for example, can administer therapy to treatment area 160 of person 156. It should be understood that electro-optical tissue stimulator 110 can be used by either the individual desiring therapy or by another person to deliver therapy to treatment area 160 of person 156. FIG. 6 shows a specific embodiment of treatment area 160 on the upper shoulder area of body 158. It is to be understood that treatment area 160 can be any size or shape and have any placement on body 158, depending on the specifics of the condition to be treated.

Pain reduction occurs in the area of tissue 166 which receives current 135 from active tip 118. Output level adjustor 116 adjusts the level of current 135 up and down, which adjusts the level of current 135 received by tissues 166 up or down accordingly. It has been found that for best pain relief results the current level should be adjusted high enough for the tissues to be affected, but not high enough to cause trauma or damage to the tissue with the electrical current. The method developed according to the invention for treating pain and administering microcurrent electrostimulation therapy is to activate microcurrent electrostimulation therapy unit 129 of electro-optical tissue stimulator 110 and then contact a test area of the body with active tip 118. The test area should be an area of the body that is not included in treatment area 160. The electrical current output level should be adjusted using power output level adjustor 116 to the lowest level where a tingling sensation can be felt in the test area in response to contact from active tip 118 and current 135 passing through tissues in the test area. The electrical current output level that just begins to create a tingling sensation in the test area is the desired electrical current output level for providing microcurrent electrostimulation therapy to treatment area 160. The desired electrical current output level is used to provide microcurrent electrostimulation therapy to treatment area 160.

The size of the area experiencing pain reduction due to microcurrent stimulation is related to the size of the area of tissue 166 receiving current 135. The geometry of electrodes 132 and 134 impacts the size of the area of tissue 166 receiving current 135, see FIG. 2 and FIG. 7. When electrodes 132 and 134 are moved closer together such that the distance $D_2$ between them is reduced, current 135 passes through a smaller area of tissue 166 when passing from one electrode to another, thus limiting the size of the area of tissue 166 receiving current 135. As the distance between electrode 132 and 135 gets larger, current 135 passes through a larger area of tissue 166 to get from one electrode to another, thereby increasing the size of the area of tissue 166 receiving current 135, which increases the size of the area of tissue receiving pain-reduction therapy. The size of the area of tissue 166 receiving pain-reduction therapy increases and decreases as the distance from electrode 132 and electrode 134 increases and decreases, respectively.

In this specific embodiment electrodes 132 and 134 are approximately ¼ inch apart. In some embodiments distance $D_2$ between electrodes 132 and 134 is larger. In other embodiments distance $D_2$ between electrodes 132 and 134 is smaller. Typically the distance $D_2$ between electrodes 132 and 134 is between ¹⁄₁₆ inch and 2 inches. The distance $D_2$ between electrode 132 and 134 is limited in some embodiments because electro-optical tissue stimulator 110 is hand-held for manual administration of therapy. Making distance $D_2$ too large would cause an undesirable increase in the size of housing 112. It is envisioned, however, that some embodiments of electro-optical tissue stimulator 110 would have remote electrodes 132 and 134. These remote electrodes 132 and 134 would be electrically connected to electro-optical tissue stimulator 110 and microcurrent source 130 via wires. This would allow electrodes 132 and 134 to be spaced a larger distance $D_2$ from each other on skin 162, thus creating a larger size area of tissue 166 receiving current 135. In these embodiments distance $D_2$ between electrodes 132 and 134 can be much larger, 12 inches, for example.

Treatment area 160 often has an area of skin 162 and underlying tissue 166 which is larger than the area which can be treated by current 135 when electro-optical tissue stimulator 110 is held stationery on skin 162. The disclosed invention includes a method of covering the entire treatment area 160 by systematically moving active tip 118 over skin 162. This is illustrated in FIG. 8 and FIG. 9. FIG. 8 and FIG. 9 show treatment area 160 which is an area of skin 162 covering tissue 166 on body 158, and two patterns of motion 172 and 173 which can be used to administer therapy to the complete treatment area 160. With electro-optical tissue stimulator 110 turned on, active tip 118 is placed against skin 162 as shown in FIG. 6 and FIG. 7. Active tip is placed at position A of treatment area 160 as shown in FIG. 8 and FIG. 9. Active tip 118 can then be moved across skin 162 in a pattern of motion 172 or 173 of FIG. 8 and FIG. 9 until position B is reached. The patterns of motion 172 and 173 can be thought of as "painting" treatment area 162 with current 135, with a goal of covering all of treatment area 162 with current 135. FIG. 8 and FIG. 9 show particular patterns of motion 172 and 173 of active tip 118 over skin 162. Many different patterns of motion are possible. In some embodiments diagonal patterns are used. In some embodiments circular patterns are used. It is to be understood that patterns are used which cover treatment area 160 and underlying tissue 166 with current 135 until the complete treatment area 160 is pain-free. In some embodiments a conductive gel is placed over skin 162 to enhance conductivity of current 135 from electrodes 132 and 134 to tissue 166 and to enhance movement of active tip 118 over skin 162.

Optical radiation therapy unit 149 provides pain relief by bathing tissue 166 with a low level of optical radiation 122. Optical radiation has been shown to reduce pain in tissues receiving the optical radiation. Optical radiation therapy as used here includes forms of therapy referred to as low level laser therapy, cold laser therapy, soft laser therapy, low energy laser therapy, and light therapy. Optical radiation therapy uses a level of optical radiation which is athermic, which means it is too low to cause tissue heating. Optical radiation therapy as discussed here does not involve tissue destruction, cauterization, vaporization, coagulation, or ablation.

Optical radiation therapy administers transcutaneous energy in the form of light to tissues of the body for remedial treatment, typically for pain reduction. Optical radiation therapy unit 149 delivers optical radiation 122 through light output port 120 mounted in active tip 118. Optical energy in the form of optical radiation 122 passes through skin 162 to tissue 166. Tissue 166 responds favorably to optical radiation 122, and the sensation of pain in tissue 166 is reduced.

In this embodiment optical radiation 122 is created by optical radiation source 150 and controlled by optical radiation controller 152, powered by battery 128. On/off switch 114 turns power on and off to optical radiation source 150, which in turn switches light beam 122 on and off, respectively. Optical radiation source 150 is on and optical radiation 122 is exiting light output port 120 when optical radiation therapy unit 149 is activated, or turned on. Optical radiation 122 passes through light output port 120 in active tip 118 and impinges on skin 162. Optical radiation 122 passes through skin 162 to tissue 166, as shown in FIG. 7. Optical radiation 122 passes some depth into tissue 166 before dissipating by absorption and scattering. The depth which optical radiation 122 reaches into tissue 166 is dependent on the power level of optical radiation 122, as well as the wavelength of optical radiation 122 and the specific type and property of tissue 166 being treated. In this way optical radiation therapy unit 149 delivers optical radiation 122 through light output port 120 mounted in active tip 118.

Output level adjustor 116 is used for adjusting the optical radiation power output level (also referred to as the optical radiation output level) of light beam 122 in this embodiment of electro-optical tissue stimulator 110. In this embodiment output level adjustor 116 and on/off switch 114 are used for both microcurrent electrostimulation therapy unit 129 for turning on and off and adjusting the electrical current output level of current 135 and optical radiation therapy unit 149 for turning on and off and adjusting the optical radiation output level of light beam 122. In some embodiments optical radiation 122 and current 135 are controlled by separate on/off switches. In some embodiments the output power of optical radiation 122 and electrical current 135 are adjusted independently using power level adjustors 115 and 117.

There are many specific embodiments of circuit implementations for optical radiation controller 152 and optical radiation source 150 known in the art, which can be used to create specific embodiments of optical radiation therapy unit 149. Optical radiation source 150 can be one or more than one light emitting device of any type. Typically optical radiation source 150 is either a laser diode or a light emitting diode. In this specific embodiment optical radiation source 150 is a single red laser diode emitting light at 770 nanometers (nm) with an emission range of plus or minus 10 nm. In some embodiments optical radiation source 150 comprises multiple light emitting devices. These multiple light emitting devices can have the same optical properties, or they can have similar optical properties, or they can have different optical properties.

Optical radiation 122 emitted by optical radiation source 150 can have many different properties as known in the art for light emitting devices. Optical radiation 122 emitted by optical radiation source 150 is characterized by the optical radiation output power level of optical radiation 122, and the specific characteristics of light which makes up optical radiation 122 such as whether the light is monochromatic or non-monochromatic, the color of the light, which is defined by the peak wavelength and wavelength range emitted, directionality of the light, divergence of the light, and coherence of the light. The specifics of optical radiation 122 are chosen based on the specific type of therapy to be provided with electro-optical tissue stimulator 110. Many different embodiments of electro-optical tissue stimulator 110 are possible which cover the range of possible characteristics of optical radiation 122. Optical radiation 122 can be composed of multiple light beams from multiple light emitting devices. These multiple light beams from multiple light emitting devices can have the same optical properties, or they can have similar optical properties, or they can have different optical properties Optical radiation 122 can be monochromatic, which means it is composed of a very small range of wavelengths of light. Lasers are often monochromatic, having a small bandwidth (width of the range of wavelengths being emitted). In this specific embodiment optical radiation 122 is monochromatic from optical radiation source 150 which is a red laser diode. In some embodiments optical radiation 122 is composed of monochromatic light emitted from a monochromatic light source which is a part of optical radiation source 150, and non-monochromatic light emitted from a non-monochromatic light source which is also part of optical radiation source 150. In some embodiments optical radiation source 150 includes multiple light sources, some of which are monochromatic and some of which are non-monochromatic.

Optical radiation 122 is non-monochromatic in some embodiments, having a wide bandwidth, which means a wide range of emitted light wavelengths. Light emitting diodes (LEDs) typically emit a wide range of wavelengths of light. Optical radiation 122 can be composed of more than one light beam, where the individual light beams can each be monochromatic or non-monochromatic.

The peak wavelength of optical radiation 122 can vary among those known in the art. The peak wavelength usually defines the color of emitted light. Some common wavelengths used are red or near-infrared in color, with peak wavelengths ranging from 632.8 nm when a helium-neon laser is used, to 660 and 670 nm for other laser diodes, and 810 nm which is emitted from a gallium aluminum arsenide (GaAlAs) semiconductor laser. A common range of wavelengths to use for optical radiation therapy is 735 to 780 nm. A light emitting device with any one or more than one of these peak wavelengths or wavelength ranges can be used as optical radiation source 150 in electro-optical tissue stimulator 110 according to the invention.

Other wavelength and wavelength ranges are also possible for use in embodiments of electro-optical tissue stimulator 110 according to the invention. Lasers, laser diodes, and LEDs are available which emit light in the ultraviolet spectrum (wavelengths smaller than 400 nm), the blue spectral range (wavelengths around 440 nm), the green spectral range (wavelengths around 540 nm) and other colors and ranges in between. The wavelength of optical radiation 122 is chosen based on the type of treatment needed, the type of tissue to be treated, and the power level desired. Optical radiation 122 can have a wavelength spectrum with multiple peaks, as when optical radiation 122 is composed of light beams from multiple optical radiation sources 150, and each source has a different peak wavelength. These different wavelengths can be used to administer different types of treatment, for example.

In some embodiments of electro-optical tissue stimulator 110 according to the invention, electro-optical tissue stimulator 110 includes wavelength adjustor 154. Wavelength adjustor 154 is included with some embodiments of electro-optical tissue stimulator 110 in which optical radiation source 150 can emit different wavelengths of light, and the particular wavelength of light emitted is adjustable. In this case wavelength adjustor 154 adjusts the wavelength of light emitted by electro-optical tissue stimulator 110. Wavelength adjustor 154 is used to set the wavelength of optical radiation 122 delivered by electro-optical tissue stimulator 110.

The level of benefit obtained from optical radiation therapy unit 149 can depend on the level of absorption of optical radiation 122 by tissue 166. Higher levels of absorption lead to increased pain reduction. Some particular types of tissue absorb specific wavelength more or less than other wavelengths, and so the wavelength chosen for optical radiation 122 can depend on the type of tissue to be treated. Additionally, the power consumed by optical radiation source 150 can depend on the specific wavelengths of light emitted. Wavelengths in the blue and green spectral ranges typically require higher power consumed by optical radiation source 150. For battery powered devices, therefore, the red and near-infrared spectral ranges are often used.

Optical radiation 122 can be directional or non-directional, which refers to the extent to which optical radiation 122 diverges after it leaves light output port 120. The amount of divergence of optical radiation 122 determines how wide an area of skin 162 optical radiation 122 covers. Lasers often emit directional light, for example, resulting in a small area of skin 162 covered by optical radiation 122. Optical radiation 122 emitted from a laser, as in this embodiment where optical radiation 122 is from a red laser diode, is typically a narrow beam several mm to 10 to 20 mm in diameter, and does not get much larger (diverge) as optical radiation 122 travels away from active tip 118. This means that the size of the area of skin 162 and tissue 166 radiated by optical radiation 122 from a laser is relatively small in size. LEDs emit light that is less directional. Optical radiation 122 that is emitted from an LED will diverge after exiting light output port 120, which means that a larger area of skin 162 and tissue 166 is radiated by optical radiation 122 than is the case with laser emission. In some embodiments optics are used at light output port 120 to make optical radiation 122 more or less directional. A narrow light beam 122 irradiating a smaller area of skin 162 and tissue 166 will mean a smaller area of tissue 166 receives optical radiation treatment at any point in time, but the tissue irradiated will receive a higher level of optical radiation power, resulting in a higher level of pain reduction. A wider, more divergent light beam 122 irradiating a larger area of skin 162 and tissue 166 will mean a larger area of tissue 166 receives optical radiation treatment at any point in time, but the tissue irradiated will receive a lower level of optical radiation power, resulting in a lower level of pain reduction. In some embodiments adjustable optics are used in active tip 118 so that the size of optical radiation 122 and the resulting size of the area of tissue 166 receiving optical radiation therapy can be adjustable. In some embodiments optical radiation 122 can be composed of both directional and non-directional light beams, as when multiple optical radiation sources 150 are used, and the individual optical radiation sources 150 have different directionality characteristics.

Optical radiation 122 can be coherent or incoherent. Coherence refers to the level of organized relationship between emitted light waves. Lasers often emit coherent light, and LEDs often emit incoherent light. Either coherent or incoherent light can comprise optical radiation 122 in embodiments of electro-optical tissue stimulator 110 according to the invention, according to the specific condition to be treated or type of treatment desired. In some embodiments of electro-optical tissue stimulator 110, optical radiation 122 can be composed of both coherent and incoherent light.

Optical radiation 122 has an optical radiation power output level (optical radiation output level) low enough to provide athermal therapy, meaning no tissue heating. This means optical radiation 122 has an output power less than 1 watt. Typical levels of optical radiation output power for optical radiation therapy are between 5 and 100 milliwatts (mw). Optical radiation 122 can be pulsed light or non-pulsed, frequency modulated or non-frequency modulated. In some embodiment electro-optical tissue stimulator 110 includes optical radiation duty cycle adjustor 153. Optical radiation duty cycle adjustor 153 adjusts the duty cycle of optical radiation 122 delivered by optical radiation therapy unit 149. The duty cycle is the relative time that optical radiation 122 is "on" compared to the sum of the time optical radiation 122 is "on" and the time optical radiation 122 is "off". Therefore, optical radiation duty cycle adjustor 153 adjusts the time optical radiation 122 is "on" compared to the time optical radiation 122 is "off" for optical radiation therapy unit 149. Optical radiation duty cycle adjustor 153 is used to set the output duty cycle of optical radiation 122 delivered by electro-optical tissue stimulator 110. Its should be understood that the specific choice of characteristics for optical radiation source 150 and optical radiation 122 are based on the specific type of treatment desired and the tissue to be treated, as is known in the art. Any of the varieties and specifics discussed can be used in the invention disclosed herein.

In some embodiments electro-optical tissue stimulator 110 includes output phase adjustor 124, which adjusts the relative phase of electrical current 135 and optical radiation 122 delivered by electro-optical tissue stimulator 110. Output phase adjustor 124 is used in those embodiments of electro-optical tissue stimulator 110 where both electrical current 135 and optical radiation 122 can be pulse-width modulated and have their duty cycles adjusted. Output phase adjustor 124 is used to adjust (set) the relative phase of electrical current 135 pulses with respect to optical radiation 122 pulses. For example, if both electrical current 135 and optical radiation 122 are set to a 50 percent duty cycle, they will both be "on" half the time, and "off" half the time. Using output phase adjustor 124 they can be adjusted so they are both "on" at the same time, and both "off" at the same time. Or, alternatively, output phase adjustor 124 can be set so electrical current 135 is "on" while optical radiation 122 is "off" and vice versa. Or, alternatively, output phase adjustor 124 can be set to any phase difference in between those two examples. Output phase adjustor 124 of electro-optical tissue stimulator 110 is used to set the relative phase of electrical current 135 and optical radiation 122 delivered by electro-optical tissue stimulator 110.

The level of pain reduction obtained from optical radiation therapy unit 149 is related to the optical radiation power output level of optical radiation 122. Pain reduction occurs in the area of tissue which receives optical radiation 122. The higher the optical radiation output power level of optical radiation 122, the larger the area of tissue 166 receiving optical radiation 122 because the depth of penetration of optical radiation 122 into tissue 166 is directly related to the optical radiation power output level of optical radiation 122. In addition, the higher the optical radiation power output level of optical radiation 122 the higher the level of irradiation received by tissue 166. Output level adjustor 116 is provided on electro-optical tissue stimulator 110 for adjusting the optical radiation power output level (also referred to as the optical radiation output level or optical power level) of optical radiation 122. Adjusting the optical radiation output level of optical radiation 122 up or down increases or decreases, respectively, the level of pain reduction obtained from optical radiation therapy administered by electro-optical tissue stimulator 110. The level of pain reduction obtained by person 156 due to optical radiation therapy administered by electro-optical tissue stimulator 110 is increased or decreased in response to the optical radiation output level of optical radiation 122 being increased or decreased, respectively. In some embodiments the optical radiation output level is adjusted using an adjustor other than output level adjustor 116.

The level of pain reduction obtained from optical radiation therapy unit 149 is related to the size of the area of skin 162 receiving optical radiation 122. The size of the area of skin 162 receiving optical radiation 122 is determined by the diameter of optical radiation 122 on skin 162, which in turn can depend on the distance from active tip 118 to skin 162. In this specific embodiment active tip 118 is held against skin 162, which means the area of skin 162 receiving optical radiation 122 can be relatively small. In other embodiments light beam 122 can be placed in an emitter remote from but electrically connected to active tip 118 so that the distance from light output port 120 to skin 162 is larger, allowing an increase in the size of optical radiation 122 on skin 162, making the size of the area of tissue 166 receiving treatment larger.

When active tip 118 is held against skin 162, as shown in FIG. 6 and FIG. 7, optical radiation 122 will pass through skin 162 and into tissue 166, irradiating tissue 166 with optical radiation 122 and relieving pain. Tissue 166 undergoes a reduction in the sensation of pain in response to receiving optical radiation 122. In this embodiment optical radiation source 150 is a red laser diode, which outputs a collimated narrow light beam 122. Light beam 122 from the red laser diode in this embodiment is a narrow beam of light with a small amount of divergence. This results in optical radiation 122 penetrating fairly deep into tissue 166 but the width of the area of tissue 166 receiving optical radiation 122 is not very wide. In order to irradiate all of treatment area 160 with optical radiation it may be necessary to move active tip 118 around in a systematic pattern as shown in FIG. 8 and FIG. 9. FIG. 8 and FIG. 9 shows two examples of patterns of motion 172 and 173 of active tip 118 to cover treatment area 160 with optical radiation 122. Active tip 118 is placed at position A of treatment area 160 as shown in FIG. 8 and FIG. 9. Active tip 118 is then moved across skin 162 in pattern of motion 172 of FIG. 8 or 173 of FIG. 9 until position B is reached. The patterns of motion 172 and 173 can be though of as "painting" treatment area 162 with optical radiation 122, with a goal of covering all of treatment area 162 with optical radiation 122. FIG. 8 and FIG. 9 show particular patterns of motion 172 and 173 of active tip 118 over skin 162. Many different patterns of motion are possible. In some embodiments diagonal patterns are used. In some embodiments circular patterns are used. The particular pattern used can depend on the size and shape of treatment area 160. It is to be understood that patterns are used which cover treatment area 160 and underlying tissue 166 with optical radiation 122 until the complete treatment area 160 is pain-free. In some embodiments a conductive gel is placed over skin 162 to enhance movement of active tip 118 over skin 162.

Myofascial tissue release therapy is a form of soft tissue massage which involves applying pressure to the fascia, which is a web of tissue that interconnects muscles, bones, and organs. Applying pressure to the fascia has been shown to reduce pain and increase range of motion in the body. Active tip 118 is used to apply pressure 148 (see FIG. 7) to the fascia using a massaging motion with active tip 118 over skin 162. As shown in FIG. 1 through FIG. 4, active tip 118 has top surface 125, first and second side surfaces 126 and 127, and bottom surface 128. Active tip 118 also includes flat face 140 and pointed end 145 for applying pressure 148 to skin 162 and underlying tissue 166. Top surface 125 is longer than bottom surface 128, creating angled front face 140 and pointed end 145. The tilt in flat face 140 allows for more even pressure 148 to be applied to tissues 166. Transition surface 144 is the beveled or rounded surface placed at the transition between flat face 140 and top surface 125, bottom surface 128, and first and second side surfaces 126 and 127. Transition surface 144 allows active tip 118 to slide smoothly across skin 162 during myofascial tissue release therapy. Active tip 118 is placed against skin 162 as shown in FIG. 6 and FIG. 7. Pressure 147 is applied to active tip 118 manually, which in turn applies pressure 148 to skin 162 and tissue 166. Tissue 166 that is fascia tissue experiences a reduction in pain in response to pressure 148 applied by active tip 118. Flat face 140 is used for applying pressure over a wide area, while pointed end 145 is used for applying a higher level of pressure to a smaller area. In this way active tip 118 is shaped for administering myofascial tissue release therapy. Pointed end 145 has angle 146 (See FIG. 3), which in this embodiment is about 70 degrees. Angle 146 can range from 5 to 175 degrees. Typically angle 146 is between 20 and 95 degrees, preferably between 50 and 80 degrees.

Active tip 118 may need to be moved over treatment area 160 to apply pressure 148 to the complete treatment area 160. Patterns of motion 172 and 173 shown in FIG. 8 and FIG. 9 can be used to cover treatment area 160 with pressure 148 as explained earlier. In some embodiments other patterns of motion are used. In some embodiments circular patterns are used. In some embodiments a conductive gel is placed over skin 162 to enhance movement of active tip 118 over skin 162.

It can be seen that electro-optical tissue stimulator 110 can be used to apply multiple forms of pain-relief and remedial therapy to a body by contacting skin 162 of treatment area 160 with active tip 118. In some embodiments active tip 118 is moved around on skin 162 to cover treatment area 160. Microcurrent electrostimulation therapy can be administered by active tip 118. Optical radiation therapy can be administered by active tip 118. Myofascial tissue release therapy can be administered by active tip 118. These types of therapy can be administered simultaneously, individually or in specific pairs. The specific types of therapy administered together or separately will depend on the details of treatment to be provided. Musculo-skeletal therapy is administered in the form of microcurrent electrostimulation therapy, optical radiation therapy, and/or myofascial tissue release therapy in response to the use of electro-optical tissue stimulator 110 on tissue 166 of body 158. Pain relief therapy is administered in the form of microcurrent electrostimulation therapy, optical radiation therapy, and/or myofascial tissue release therapy in response to the use of electro-optical tissue stimulator 110 on treatment area 160 of body 158.

In some embodiments of other forms of therapy can be administered with electro-optical tissue stimulator 110. Traditional muscle massage therapy can be administered with active tip 118. In some embodiments electro-optical tissue stimulator 110 is designed to provide ultrasound therapy through active tip 118. In some embodiments electro-optical tissue stimulator 110 is designed to administer heat therapy through active tip 118. Other forms of therapy can be provided by including their capabilities in electro-optical tissue stimulator 110 and active tip 118.

A method of treating pain is disclosed herein as shown in FIG. 10. Method of treating pain 310 is illustrated, which includes step 312, identifying a treatment area of a body to receive electro-optical tissue stimulation therapy. Method 310 also includes step 314 activating an electro-optical tissue stimulator, wherein the electro-optical tissue stimulator comprises an active tip. Method 310 also includes step 316 contacting a test area of the body with the active tip, wherein the test area of the body is not a part of the treatment area of the body and step 318 setting the power output level of the electro-optical tissue stimulator at a level where the test area of the body begins to feel a tingling sensation in response to contact from the active tip. Method 320 also includes step 320, contacting the treatment area with the active tip, wherein the treatment area receives microcurrent electrostimulation therapy, optical radiation therapy, and myofascial tissue release therapy in response to contact by the active tip. In some embodiments method 310 of treating pain includes other steps. In some embodiments of method 310 the portion of the treatment area which receives microcurrent electrostimulation therapy overlaps the portion of the treatment area which receives optical radiation therapy. In some embodiments of method 310 the portion of the treatment area which receives microcurrent electrostimulation therapy does not overlap the portion of the treatment area which receives optical radiation therapy.

Step 312 identifying a treatment area on a body to receive electro-optical tissue stimulation therapy can include many different steps. For instance, step 312 can include obtaining a prescription from a doctor for receiving electro-optical tissue stimulation therapy for an area of the body that is in pain. This step could include a person realizing that a portion of their body is in pain. Step 312 could include the person receiving an exam by a doctor, who identifies the treatment area and then prescribes electro-optical tissue stimulation therapy to relieve the pain.

Step 312 can include a veterinarian prescribing electro-optical tissue stimulation therapy for an area of an animal's body. While electro-optical tissue stimulator 110 is designed primarily for use on a human body, the type of therapy it delivers has been shown to provide benefits to animals also. It is therefore envisioned that therapy can be provided to animal bodies with the electro-optical tissue stimulator. Step 312 can therefore include a veterinarian or animal owner identifying a treatment area on an animal's body to receive electro-optical tissue stimulation therapy.

Step 312 can include a person realizing that an area of their body is in pain and needs therapy administered by the electro-optical tissue stimulator. It is envisioned that the electro-optical tissue stimulator can be obtained for at-home use by individuals desiring therapy. This step includes in some embodiments a person obtaining therapy by a professional, either a doctor or therapist. The doctor or therapist could identify the treatment area and the fact that electro-optical tissue stimulation therapy is advised, and administer initial treatment with the electro-optical tissue stimulator. Once the treatment is shown effective on the treatment area and the person is trained in administering therapy to themselves, this step could include the person purchasing an electro-optical tissue stimulator for home use. At that point the person could identify the treatment area on their own body to receive electro-optical tissue stimulation therapy.

Step 314 of method 310 of treating pain according to the invention comprises activating an electro-optical tissue stimulator, wherein the electro-optical tissue stimulator comprises an active tip. The active tip is capable of administering microcurrent electrostimulation therapy when activated and placed against the skin of a treatment area. The active tip is capable of administering optical radiation therapy when activated and placed where the optical radiation falls on the skin of the treatment area. The active tip is capable of myofascial tissue release therapy when used to apply pressure to the skin of the treatment area. In some embodiments the active tip is designed to administer other forms of therapy, such as ultrasound therapy, heat therapy, or muscle massage therapy.

In some embodiments step 314 activating the electro-optical tissue stimulator includes turning on a single on/off power switch. The electro-optical tissue stimulator and all of its electrical components are activated in response to turning on the single power switch in this embodiment. This single on/off power switch can provide power to all of the powered units in the electro-optical tissue stimulator, including the microcurrent electrostimulation therapy unit and the optical radiation therapy unit. In some embodiments the microcurrent electrostimulation therapy unit includes a microcurrent controller and a microcurrent source, which receives power in response to the on/off power switch being turned on to provide power to the electro-optical tissue stimulator. In some embodiments other electrical components comprising the microcurrent electrostimulation therapy unit receive power in response to activating the electro-optical tissue stimulator. The optical radiation therapy unit includes, in some embodiments, an optical radiation controller and an optical radiation source, which will receive power in response to the on/off power switch being turned on to provide power to the electro-optical tissue stimulator. In some embodiments other electrical components comprising the optical radiation therapy unit receive power in response to activating the electro-optical tissue stimulator.

In some embodiments of electro-optical tissue stimulator 110, the individual therapy units contained in electro-optical tissue stimulator 110 that require power will have their own individual power switches. In these embodiments, step 314 activating an electro-optical tissue stimulator can comprise turning on one or more than one power switches. In some embodiments step 314 includes deciding which units should be powered and which should be unpowered, and turning on the power switch for those devices or units to be powered, and leaving the power switch off for those devices or units to be left unpowered. For example, in an embodiment where microcurrent electrostimulation therapy unit 129 has its own power switch, as does optical radiation therapy unit 149, step 314 includes deciding to power (activate) microcurrent electrostimulation therapy unit 129 while leaving optical radiation therapy unit 149 unpowered. Step 314 would include, in that embodiment, turning on the power switch for the microcurrent electrostimulation therapy unit and leaving the power switch for the optical radiation therapy unit turned off. In some embodiments step 314 includes turning on the power switches for both therapy units. In some embodiments step 314 includes deciding to power (activate) optical radiation therapy unit 149 while leaving microcurrent electrostimulation therapy unit 129 unpowered. Depending on the type of therapy devices and units included in the specific embodiment of electro-optical tissue stimulator 110 and the type of therapy desired, step 314 can include turning power on to one or more individual therapy units or multiple therapy units or all the therapy units and devices included in the specific embodiment of electro-optical tissue stimulator 110. In some embodiments of electro-optical tissue stimulator 110, optical radiation source 150 comprises multiple light emitting devices. These individual light emitting devices can have their own individual power switch. In some embodiments step 314 includes turning on individual light emitting devices separately.

Method 310 according to the invention includes step 316 contacting a test area of the body with the active tip, wherein the test area of the body is not a part of the treatment area of the body. In this step the active tip of the electro-optical tissue stimulator is placed on a test area of the body so that the power output level of the electro-optical tissue stimulator can be set. The active tip is delivering electrical current or optical radiation, or both, upon contact between the active tip and the test area of the body. A test area of the body is used to set the power output level because the treatment area is usually less sensitive to electrical current and optical radiation therapy, and so it is desirable to use a test area of the body which is more sensitive and allows setting the output level at the lowest level where treatment can be felt before applying this output level to the treatment area. Setting the power output level to a level just above the sensation of tingling outside the treatment area is a good starting point for setting the power level for the treatment area. In some embodiments of method 310, step 316 includes other steps.

Step 318 of method 310 of treating pain according to the invention includes setting the power output level of the electro-optical tissue stimulator at a level where the test area of the body begins to feel a tingling sensation in response to contact from the active tip. In some embodiments step 318 includes using an output level adjustor of the electro-optical tissue stimulator to adjust the power output level of the electro-optical tissue stimulator. In some embodiments the output level adjustor will adjust both the optical radiation output level and the electrical current output level. Setting the power output level of the electro-optical tissue stimulator includes adjusting the power output level and monitoring the response felt by the test area of the body. If no tingling sensation is felt, the power output level is adjusted higher. If a strong tingling sensation is felt, the power output level is adjusted down. Adjustments are made to the power output level until a level is reached where a tingling sensation is just beginning to be felt in the test area in response to the test area receiving electrical current or optical radiation, or both, from the active tip. The power output level is set at that level where the tingling sensation is just beginning to be felt. Just beginning to be felt means that if the power output level is turned down slightly, the tingling sensation stops, in other words the power output level is at the minimum power output level where a tingling response can be felt in the test area.

Step 320 of method 310 of treating pain includes contacting the treatment area with the active tip, wherein the treatment area receives microcurrent electrostimulation therapy, optical radiation therapy, and myofascial tissue release therapy in response to contact by the active tip. Now that the power output level has been set in step 318, step 320 includes contacting the treatment area with the active tip to provide treatment. Step 320 can include administering these forms of therapy simultaneously or individually or in pairs depending on the specifics of the therapy to be administered. Step 320 can include administering other forms of therapy in addition to microcurrent electrostimulation therapy, optical radiation therapy, and myofascial release therapy, depending on the specific types of therapy desired and the specific embodiment of electro-optical tissue stimulator 110. In some embodiments step 320 include adjusting the power output level up or down as needed.

Step 320 can include moving the active tip in a pattern of motion within the treatment area. The pattern of motion can be a linear pattern of horizontal or vertical lines as shown in FIG. 8 and FIG. 9, for example. The pattern of motion can be circular. The patterns of motion can take many different forms. The pattern of motion is designed to cover the skin and tissue of the treatment area with electrical current, optical radiation, and/or pressure, and the patterns used to accomplish this will vary depending on the size and position on the body of the treatment area and the condition being treated.

Step 320 can include administering microcurrent electrostimulation therapy, optical radiation therapy, and myofascial tissue release therapy, or any of those types of therapy individually or in pairs, for a specific time period. The time period used for administering therapy can be many different time periods, but it is usually within 1 to 30 minutes. A typical time period for administering therapy is two minutes per treatment area. Other times for treatment are used depending on the specific treatment area and the type of condition being treated.

Method of treating pain 310 can include many other steps. In some embodiments method 310 includes setting the wavelength of the optical radiation delivered by the electro-optical tissue stimulator. In some embodiments of the electro-optical tissue stimulator, the optical radiation source is capable of delivering optical radiation output in a number of different wavelengths. The wavelength to be delivered can be adjusted, or set, by using a wavelength adjustor, which allows the user to adjust the wavelength of light delivered by the electro-optical tissue stimulator. This allows the wavelength to be set to one wavelength to treat a particular type of tissue or ailment, and then set to a different wavelength to treat a different type of tissue or ailment, for example. The wavelength can be varied for many different reasons. Use of the optical wavelength adjustors allows the user to set the wavelength of the optical radiation delivered by the electro-optical tissue stimulator.

In some embodiments method 310 of treating pain includes the step of setting the output duty cycle of the optical radiation delivered by the electro-optical tissue stimulator. In some embodiments the optical radiation delivered by the electro-optical tissue stimulator is pulse-width modulated such that optical radiation is delivered for some amount of time in an "on" pulse, during which optical radiation is emitted, followed by an "off" pulse, during which no optical radiation is emitted, and then the on and off pulses are repeated. The ratio of the time the optical radiation pulse is "on" compared to the total time for one "on" pulse and one "off" pulse is called the duty cycle of the optical radiation output. Some embodiments of the electro-optical tissue stimulator include an optical radiation duty cycle adjustor, which allows the user to set the output duty cycle of the optical radiation delivered by the electro-optical tissue stimulator. The optical radiation duty cycle is adjusted in order to tailor the type of treatment provided by the optical radiation therapy unit of the electro-optical tissue stimulator. Some types of tissue respond favorably to short "on" pulses of optical radiation (a small duty cycle). Other types of tissue response better to long "on" pulses of optical radiation (a large duty cycle). The use of the optical radiation duty cycle adjustor allows the user to tailor the optical radiation therapy performed by the electro-optical tissue stimulator for a particular type of tissue or treatment desired.

In some embodiments method 310 of treating pain includes the step of setting the output duty cycle of the electrical current delivered by the electro-optical tissue stimulator. In some embodiments the electrical current delivered by the electro-optical tissue stimulator is pulse-width modulated such that electrical current is delivered for some amount of time in an "on" pulse, during which electrical current is emitted, followed by an "off" pulse, during which no electrical current is emitted, and then the on and off pulses are repeated. The ratio of the time the electrical current pulse is "on" compared to the total time for one "on" pulse and one "off" pulse is called the duty cycle of the electrical current output. Some embodiments of the electro-optical tissue stimulator include an electrical current duty cycle adjustor, which allows the user to set the output duty cycle of the electrical current delivered by the electro-optical tissue stimulator. The electrical current duty cycle is adjusted in order to tailor the type of treatment provided by the microcurrent electrostimulation therapy unit of the electro-optical tissue stimulator. Some types of tissue respond favorably to short "on" pulses of electrical current (a small duty cycle). Other types of tissue response better to long "on" pulses of electrical current (a large duty cycle). The use of the electrical current duty cycle adjustor allows the user to tailor the microcurrent electrostimulation therapy performed by the electro-optical tissue stimulator for a particular type of tissue or treatment desired.

In some embodiments method 310 includes setting the relative phase of the optical radiation and electrical current delivered by the electro-optical tissue stimulator. Setting the relative phase of the electro-optical tissue stimulator is done with the output phase adjustor of the electro-optical tissue stimulator. In those embodiment of the electro-optical tissue stimulator in which both the optical radiation and the electrical current are pulse-width modulated, the output phase adjustor sets, or adjusts, the relative starting point, in time, of the two "on" pulses, the optical radiation "on" pulse, and the electrical current "on" pulse. There are many possible results of this adjustment; one example will be discussed here. In the case where both the optical radiation and the electrical current are set to a 50 percent duty cycle, both of them are "on" for half the time and "off" for half the time. The output phase adjustor is used to set the amount of overlap in the "on" pulses. For instance, the output phase adjustor can be set such that the optical radiation is "off" when the electrical current is "on", and vice versa. Or the output phase adjustor can be set so the optical radiation is "on" simultaneously with the electrical current, or any amount of overlap between duty cycles in between those two extremes. This allows different types of therapy to be delivered, and allows the therapy provided by the electro-optical tissue stimulator to be tailored to the type of tissue and the type of tissue problem encountered.

Method 310 can include the step of recording a level of pain in the treatment area before therapy. This recordation of the level of pain can be done by either the person undergoing treatment or by a doctor or therapist, or another professional performing or overseeing treatment. Method 310 can include the step of recording a level of disability in the treatment area before therapy. The level of disability recorded can take many forms, depending on the specific problem. The level of disability recorded can include a level of movement, level of flexibility, or other forms of disability related to the problem being treated. In some embodiments other testing is included. The recordation of the level of disability can be performed by either the person undergoing treatment or by a doctor, therapist, or other professional performing or overseeing the treatment.

Method 310 can also include the steps of testing a level of disability before administering treatment, and recording the test results. The testing can be done by either the person undergoing treatment or the professional performing or overseeing the treatment. Testing performed can take many different forms, depending on the problem being treated and the specifics of the case. The testing can include testing a level of pain, disability, flexibility, range of motion, or mobility, for example. These test results can be recorded and tracked to compare with results after treatment for the purpose of determining the effectiveness of the therapy administered.

Method 310 can include applying a conductive gel to the treatment area before contacting the skin with the active tip. The amount of current transferred to tissue 166 can be increased in response to applying conductive gel to the treatment area before therapy. This is because the gel is conductive and will pass current more easily through the active tip/skin interface than without the conductive gel. The amount of optical radiation transferred to tissue 166 can be increased in response to applying conductive gel to the treatment area before therapy. This is because the gel provides a matched optical interface between active tip 118 and skin 162 and will allow more optical radiation through the active tip/skin interface than without the conductive gel. In addition, conductive gel can increase the effectiveness of the myofascial tissue release therapy administered by active tip 118 because the conductive gel is slippery and will allow active tip 118 to slide more easily over skin 162.

Method 310 can include the steps of testing a level of disability of the treatment area after administering therapy, and recording a level of pain or disability in the treatment area after administering therapy. Testing and recording the level of pain or disability after therapy is administered can be done by the person receiving treatment or by the professional administering or overseeing the treatment. The testing can include testing a level of pain, disability, flexibility, range of motion, or mobility as called for by the problem and the treatment. In some embodiments other forms of testing are included. Typically the testing done after administering therapy will match the testing performed before administering therapy to allow measuring and tracking the effectiveness of the treatment. Method 310 can therefore include measuring and tracking the effectiveness of the treatment administered by electro-optical tissue stimulator 110.

Method 310 can also include generating a schedule for further treatment. This schedule can be determined base on the subject's response to the therapy, and the results of measures of effectiveness of the treatment, if computed. A typical treatment schedule starts with a total of five treatments, each treatment lasting no more than two minutes per area. These treatments are administered daily or every other day, typically no more than five time per day. After these initial five treatments, additional treatments can be scheduled based on results. The frequency and timing of treatments can vary greatly depending on the person being treated and the condition being treated. The schedule disclosed here is one example of many possible treatment schedules.

A method of administering therapy to a body according to the invention is disclosed as shown in FIG. 11. Shown in FIG. 11 is method 340 of administering therapy to a body, which includes step 342 identifying a treatment area of a body to receive therapy from an electro-optical tissue stimulator, wherein the electro-optical tissue stimulator comprises an active tip, and step 344, determining the desired optical radiation output level of the electro-optical tissue stimulator. Method 340 also includes step 346 determining the desired electrical current output level of the electro-optical tissue stimulator and step 348 setting the optical radiation output level of the electro-optical tissue stimulator to the desired optical radiation output level. Method 340 of administering therapy to a body also includes step 352, administering myofascial tissue release therapy to the treatment area using the active tip, wherein the treatment area receives microcurrent electrostimulation therapy, optical radiation therapy, and myofascial tissue release therapy in response to administering myofascial tissue release therapy with the active tip.

Step 342 identifying a treatment area of a body to receive therapy from an electro-optical tissue stimulator, wherein the electro-optical tissue stimulator comprises an active tip, can include many steps. Step 342 can include an individual identifying a treatment area on their own body to receive therapy from an electro-optical tissue stimulator. Step 342 can include a doctor or therapist identifying a treatment area on a patient's body to receive therapy with an electro-optical tissue stimulator. Step 342 can include obtaining a prescription from a doctor for receiving electro-optical tissue stimulation therapy for an area of the body that is in pain. Step 342 could include the person receiving an exam by a doctor, who identifies the treatment area and then prescribes therapy from an electro-optical tissue stimulator with an active tip to relieve the pain.

Step 342 can include a veterinarian prescribing electro-optical tissue stimulation therapy for an area of an animal's body. In some embodiments step 342 can include a person realizing that an area of their body is in pain and needs therapy administered by the electro-optical tissue stimulator with an active tip. It is envisioned that the electro-optical tissue stimulator can be obtained for at-home use by individuals desiring therapy. This step includes in some embodiments a person obtaining therapy by a professional, either a doctor or therapist. The doctor or therapist could identify the treatment area and the fact that electro-optical tissue stimulation therapy is advised, and administer initial treatment with the electro-optical tissue stimulator. Once the treatment is shown effective on the treatment area and the person is trained in administering therapy to themselves, this step could include the person purchasing an electro-optical tissue stimulator for home use. At that point the person could identify the treatment area on their own body to receive electro-optical tissue stimulation therapy.

Step 344 determining the desired optical radiation output level of the electro-optical tissue stimulator can include many other steps. The desired optical radiation output level is the level of optical radiation being delivered by the active tip of the electro-optical tissue stimulator that will be initially used to administer optical radiation therapy. It is desirable to start administering therapy to the treatment area with a level of optical radiation that is high enough to obtain pain relief results, and yet not high enough to cause the treatment area to response too quickly or react with an increase in pain. A slow response from the treatment area is desired, with just enough optical radiation to stimulate the tissues into repair mode. It is desirable to stimulate the treatment area into repair over several sessions of low radiation treatment as opposed to shorter treatments with higher levels that may cause an over-reaction from the tissues. In some embodiments of the invention step 344 includes the step of setting the electrical current output level of the electro-optical tissue stimulator to zero. This allows the user to find the desired optical radiation output level without being confused by electrical current causing a response in the tissues also. In some embodiments setting the electrical current output level of the electro-optical tissue stimulator to zero is done using the electrical current output level adjustor of the electro-optical tissue stimulator to adjust the level of electrical current delivered by the microcurrent electrostimulation therapy unit to zero. In some embodiments of method 340, step 344 includes the additional step of contacting a test area of the body with the active tip, wherein the test area is not included in the treatment area. This is done because an area of the body outside the treatment area is often more sensitive to optical radiation treatment than the treatment area. The treatment area is usually in pain and less sensitive to therapy. For this reason a test area of the body is used to find the desired optical radiation output level, then this level can be used as a starting point for treatment to the treatment area. In some embodiments step 344 includes the step of adjusting the optical radiation output level until the desired optical radiation output level of the electro-optical tissue stimulator is determined, wherein the desired optical radiation output level is that level where a tingling sensation is beginning to be felt in the test area in response to the test area receiving optical radiation from the active tip. This step involves finding that level of optical radiation that just begins to cause a tingling response in the test area. This often includes the step of turning the level of optical radiation output up and down to identify that level below which no tingling sensation is felt in the test area. In some embodiments adjusting the optical radiation output level of the electro-optical tissue stimulator is done using the optical radiation output level adjustor of the electro-optical tissue stimulator to adjust the level of optical radiation delivered by the optical radiation therapy unit. The level of optical radiation where a tingling sensation is just beginning to be felt is defined as the desired optical radiation output level of the electro-optical tissue stimulator and is used as the level for beginning therapy on the treatment area. In some embodiments step 344 includes writing down or otherwise storing or marking the desired optical radiation output level so that this level can be returned to easily.

Step 346 of method 340 according to the invention can include many other steps. In some embodiments step 346 determining the desired electrical current output level of the electro-optical tissue stimulator includes the step of setting the optical radiation output level of the electro-optical tissue stimulator to zero. After the desired optical radiation output level has been determined and noted, it is time to determine the desired electrical current output level and this is often done with the optical radiation output level set to zero so finding the desired electrical current output level does not get confused by optical radiation output from the active tip. In some embodiments setting the optical radiation output level of the electro-optical tissue stimulator to zero is done using the optical radiation output level adjustor of the electro-optical tissue stimulator to adjust the level of optical radiation delivered by the optical radiation therapy unit to zero. In some embodiments of method 340, step 346 includes the step of contacting a test area of the body with the active tip, wherein the test area is not included in the treatment area. This is done for the same reasons as discussed in step 344 above. In some embodiments step 346 includes the step of adjusting the electrical current output level until the desired electrical current output level of the electro-optical tissue stimulator is determined, wherein the desired electrical current output level is that level where a tingling sensation is beginning to be felt in the test area in response to the test area receiving electrical current from the active tip. This step involves finding that level of electrical current that just begins to cause a tingling response in the test area. This often includes turning the level of electrical current output up and down to identify that level below which no tingling sensation is felt in the test area. In some embodiments adjusting the electrical current output level of the electro-optical tissue stimulator is done using the electrical current output level adjustor of the electro-optical tissue stimulator to adjust the level of electrical current delivered by the microcurrent electrostimulation unit. The level of electrical current where a tingling sensation is just beginning to be felt is defined as the desired electrical current output level of the electro-optical tissue stimulator and is often used as the level for beginning therapy on the treatment area. In some embodiments step 346 includes writing down or otherwise storing or marking the desired electrical current output level so that this level can be returned to easily. In some embodiments this step involves leaving the electrical current output level of the electro-optical tissue stimulator at the desire electrical current output level in order to begin therapy at the desired electrical current output level.

Step 348 setting the optical radiation output level of the electro-optical tissue stimulator to the desired optical radiation output level can include many other steps. This step is where the output level, which was set to zero in order to determine the desired electrical current output level, is set back to the previously-determined desired optical radiation output level so that therapy on the treatment area can begin. In some embodiments the optical radiation output level adjustor of the electro-optical tissue stimulator is used to adjust the optical radiation output level to the desired optical radiation output level which was determined earlier.

Step 352 administering myofascial tissue release therapy to the treatment area using the active tip, wherein the treatment area receives microcurrent electrostimulation therapy, optical radiation therapy, and myofascial tissue release therapy in response to administering myofascial tissue release therapy with the active tip, can include many other steps. Step 352 can include applying a conductive gel to the treatment area before administering therapy.

Method 340 can include many other steps, including administering other types of therapy which a specific embodiment of electro-optical tissue stimulator 110 is designed to provide, including ultrasound therapy, heat therapy, or massage therapy. In some embodiments method 340 includes setting the wavelength of the optical radiation delivered by the electro-optical tissue stimulator. In some embodiments of the electro-optical tissue stimulator, the optical radiation source is capable of delivering optical radiation having a number of different wavelengths. The wavelength to be delivered can be adjusted, or set, by using a wavelength adjustor, which allows the user to adjust the wavelength of light delivered by the electro-optical tissue stimulator. This allows the wavelength to be set to one wavelength to treat a particular type of tissue or ailment, and then set to a different wavelength to treat a different type of tissue or ailment, for example. The wavelength can be varied for many different reasons. Use of the optical wavelength adjustors allows the user to set the wavelength of the optical radiation delivered by the electro-optical tissue stimulator.

In some embodiments method 340 includes the step of setting the electrical current output level of the electro-optical tissue stimulator to the desired electrical current output level. The power output level adjustor of the electro-optical tissue stimulator which adjusts the electrical current level up and down is used to adjust the electrical current output level to the desired electrical current output level.

In some embodiments method 340 of administering therapy to a body includes the step of setting the frequency of the electrical current output of the electro-optical tissue stimulator. In some embodiments the electro-optical tissue stimulator includes an electrical current frequency adjustor, which is an apparatus which allows the frequency of the electrical current delivered by the microcurrent electrostimulation therapy unit to be adjusted within a range of available frequencies. Adjusting the frequency of the electrical current delivered can change the specific treatment delivered by the electro-optical tissue stimulator.

In some embodiments method 340 includes setting the relative phase of the optical radiation and electrical current delivered by the electro-optical tissue stimulator. Setting the relative phase of the electro-optical tissue stimulator is done with the output phase adjustor of the electro-optical tissue stimulator, as explained earlier. Setting the relative phase of the optical radiation and electrical current delivered by the electro-optical tissue stimulator allows different types of therapy to be delivered, and allows the therapy provided by the electro-optical tissue stimulator to be tailored to the type of tissue and the type of problem.

In some embodiments method 340 includes the steps of recording a level of pain, disability, flexibility, range of motion or mobility in the treatment area before administering therapy. Method 340 can also include the steps of testing a level of pain, disability, flexibility, range of motion or mobility before administering treatment. In some embodiments method 340 includes the steps of testing and/or recording a level of pain, disability, flexibility, range of motion, or mobility after administering therapy. Method 340 can in some embodiments include comparing the level of pain, disability, flexibility, range of motion or mobility after treatment to that received before treatment. Method 340 can include the step of using the data obtained from before and after testing to compute the efficiency of treatments and/or the treatment schedule.

Disclosed herein is a method of doing business shown in FIG. 12. FIG. 12 illustrates method 270 of conducting business comprising step 276 developing techniques for providing therapy utilizing an electro-optical tissue stimulator, step 280 marketing the electro-optical tissue stimulator, and step 284 selling the electro-optical tissue stimulator to doctors and patients.

Method 270 can include many other steps. For example, in some embodiments method 270 includes designing an electro-optical tissue stimulator. In some embodiments method 270 can include obtaining government approval for using and selling the electro-optical stimulator. Method 270 can include paying doctors for their time spent teaching the use of the electro-optical stimulator. In some embodiments method 270 includes paying doctors for their time spent teaching other doctors to use the electro-optical tissue stimulator. In some embodiments method 270 includes paying doctors for their time spent teaching patients how to use the electro-optical tissue stimulator.

Method 270 can include the step of manufacturing an electro-optical tissue stimulator. Manufacturing an electro-optical tissue stimulator can itself include many different steps, including design optimization and changes, producing individual components and/or locating sources for the individual components, assembling the electro-optical tissue stimulator and testing the electro-optical tissue stimulator. Method 270 may include manufacturing different embodiments of electro-optical tissue stimulators, including embodiments for doctors to use, embodiments for patients to use at home, embodiments which include more power output capability or less power output capability, embodiments which are smaller or larger for particular specific treatments, embodiments for use on animals, and embodiments which include the capability to administer fewer or greater number of types of therapy.

Step 276 developing techniques for providing therapy utilizing the electro-optical tissue stimulator can include many different steps. Step 276 can include treating patients using different techniques and tracking the efficiency of the different techniques. In some embodiments step 276 includes obtaining feedback from patients and other professionals administering therapy with an electro-optical tissue stimulator. Step 276 can also include conducting studies to measure the efficiency of different techniques of administering therapy with the electro-optical tissue stimulator. These studies can be done by the individual or entity conducting business method 270 or contracted to an outside entity.

Step 280 marketing the electro-optical tissue stimulator can include many different steps. Step 280 can include the steps of creating marketing materials, distributing the marketing materials to doctors, therapists, and individuals, creating a website promoting the electro-optical tissue stimulator, and selling starter packs which includes a number of electro-optical tissue stimulators and information about them. Step 280 can include any activities included in distributing information about the electro-optical tissue stimulator with the intent to inform doctors and patients and increase the level of understanding and visibility of the electro-optical tissue stimulator. Step 280 can include distributing results of studies showing the effectiveness of the electro-optical tissue stimulator.

Step 284 selling the electro-optical tissue stimulator can include many different steps. Step 284 can include selling the electro-optical tissue stimulator to doctors for use in their practice. Step 284 can include selling the electro-optical tissue stimulator to therapists for use in their practice. Step 284 can include selling the electro-optical tissue stimulator to patients for individual use. Step 284 selling the electro-optical tissue stimulator can include other steps involved in transferring ownership of an electro-optical tissue stimulator and receiving payment for the electro-optical tissue stimulator.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. For example, specific therapy techniques can be developed for use with the electro-optical tissue stimulator, using the several types of therapy administered in unique steps or combinations to obtain specific results.

The invention claimed is:

1. A device for administering therapy to a body comprising:
   a housing;
   an active tip, wherein the active tip is shaped for administering myofascial tissue release therapy to a body;
   a microcurrent electrostimulation therapy unit contained in the housing, wherein the microcurrent electrostimulation therapy unit delivers electrical current through a first and a second electrode mounted in the active tip;
   an optical radiation therapy unit contained in the housing, wherein the optical radiation therapy unit delivers optical radiation through a light output port mounted in the active tip; and
   an output level adjustor mounted in the housing, wherein the output level adjustor allows independent adjustment of the level of electrical current delivered by the microcurrent electrostimulation therapy unit and the level of optical radiation delivered by the optical radiation therapy unit; and
   an output phase adjustor, wherein the output phase adjustor selectively adjusts a phase difference between the electrical current and the optical radiation delivered by the electro-optical tissue stimulator to any amount between 0 degrees and 180 degrees.

2. The device of claim 1, further comprising a wavelength adjustor, wherein the wavelength adjustor adjusts the wavelength of the optical radiation delivered by the optical radiation therapy unit.

3. The device of claim 1, further comprising an electrical current duty cycle adjustor, wherein the electrical current duty cycle adjustor sets the duty cycle of the electrical current delivered by the microcurrent electrostimulation therapy unit.

4. The device of claim 1, further comprising:
   an optical radiation duty cycle adjustor, wherein the optical radiation duty cycle adjustor adjusts the duty cycle of the optical radiation delivered by the optical radiation therapy unit; and
   an electrical current duty cycle adjustor, wherein the electrical current duty cycle adjustor sets the duty cycle of the electrical current delivered by the microcurrent electrostimulation therapy unit.

5. The device of claim 1, wherein the light output port is positioned between the first and second electrode.

6. The device of claim 1, further comprising an electrical current frequency adjustor, which adjusts the frequency of the electrical current delivered by the microcurrent electrostimulation therapy unit.

* * * * *